(12) United States Patent
Larom

(10) Patent No.: US 6,447,459 B1
(45) Date of Patent: Sep. 10, 2002

(54) DEVICE AND METHOD FOR MEASURING LUNG PERFORMANCE

(75) Inventor: Dov Larom, Paris (FR)

(73) Assignee: PDS Healthcare Products, Inc., Louisville, CO (US)

(*) Notice: Subject to any disclaimer, the term of this patent is extended or adjusted under 35 U.S.C. 154(b) by 0 days.

(21) Appl. No.: 09/545,624

(22) Filed: Apr. 7, 2000

(51) Int. Cl.⁷ .................................. A61B 5/08
(52) U.S. Cl. .............................. 600/538; 600/529
(58) Field of Search .......................... 600/538, 529

(56) References Cited

U.S. PATENT DOCUMENTS

| | | | |
|---|---|---|---|
| 2,724,969 A | 11/1955 | Bloser | 73/228 |
| 3,848,584 A | 11/1974 | Otsap | 128/2.08 |
| 4,073,189 A | 2/1978 | Draper | 73/228 |
| 4,122,842 A * | 10/1978 | Pikul | 128/2.08 |
| 4,294,262 A | 10/1981 | Williams et al. | 128/726 |
| 4,537,068 A | 8/1985 | Wrobel et al. | 73/202 |
| 4,736,750 A | 4/1988 | Valdespino et al. | 128/725 |
| 4,768,520 A * | 9/1988 | Varraux et al. | 128/725 |
| 4,905,709 A | 3/1990 | Bieganski et al. | 128/725 |
| 4,991,591 A | 2/1991 | Jones et al. | 128/719 |
| 5,058,601 A | 10/1991 | Riker | 128/725 |
| 5,107,846 A * | 4/1992 | Atlas | 128/666 |
| 5,134,890 A * | 8/1992 | Abrams | 73/861.52 |
| 5,170,798 A | 12/1992 | Riker | 128/725 |
| 5,277,195 A | 1/1994 | Williams | 128/725 |
| 5,279,163 A * | 1/1994 | D'Antonio et al. | 73/728 |
| 5,309,916 A * | 5/1994 | Hatschek | 128/672 |
| 5,383,470 A | 1/1995 | Kolbly | |
| 5,413,112 A | 5/1995 | Jansen et al. | 128/726 |
| 5,518,002 A | 5/1996 | Wolf et al. | 128/725 |
| 5,549,117 A | 8/1996 | Tacklind et al. | 128/716 |
| 5,564,432 A | 10/1996 | Thomson | 128/725 |
| 5,626,144 A | 5/1997 | Tacklind et al. | 128/725 |
| 5,704,366 A | 1/1998 | Tacklind et al. | 128/716 |
| 5,720,709 A | 2/1998 | Schnall | 60/538 |
| 5,732,709 A | 3/1998 | Tacklind et al. | 128/726 |
| 5,816,246 A | 10/1998 | Mirza | 128/726 |
| 5,839,430 A | 11/1998 | Cama | 128/200.14 |
| 5,868,681 A | 2/1999 | Schiller | 600/533 |
| 6,004,277 A | 12/1999 | Maharaj et al. | 600/538 |
| 6,010,460 A | 1/2000 | McNaughton | 600/538 |
| 6,019,731 A | 2/2000 | Harbrecht et al. | 600/532 |

FOREIGN PATENT DOCUMENTS

| | | |
|---|---|---|
| EP | 0 437 055 A1 | 7/2001 |
| GB | 2 236 395 A | 3/1991 |
| WO | WO 86/01172 | 2/1986 |
| WO | WO 87/01443 | 3/1987 |
| WO | WO 92/15246 | 9/1992 |

OTHER PUBLICATIONS

Notification of Transmittal of the International Search Report and the International Search Report from PCT/US01/11266.

* cited by examiner

Primary Examiner—Robert L. Nasser
Assistant Examiner—Patricia C. Mallari
(74) Attorney, Agent, or Firm—Sheridan Ross P.C.

(57) ABSTRACT

The flow measurement device of the present invention incorporates numerous novel features. For example, the device includes a displacement measuring device to measure the position of a movable plate member, a self-oscillation dampener to dampen oscillations of the plate member, one or more stiffening members engaging or incorporated into the plate member to increase the resonant frequency of the plate member and reduce flutter, and a conduit providing for differing directions of air flow at different points along its length to eliminate the effects of gravity on flow measurements.

82 Claims, 19 Drawing Sheets

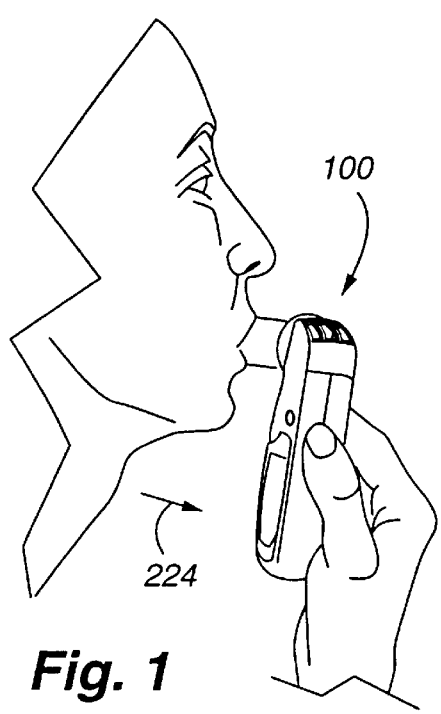
Fig. 1
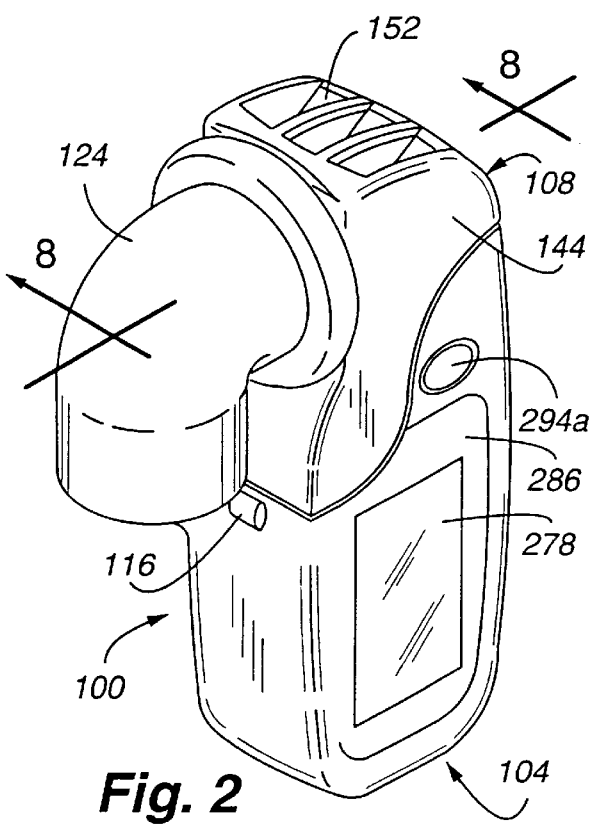
Fig. 2
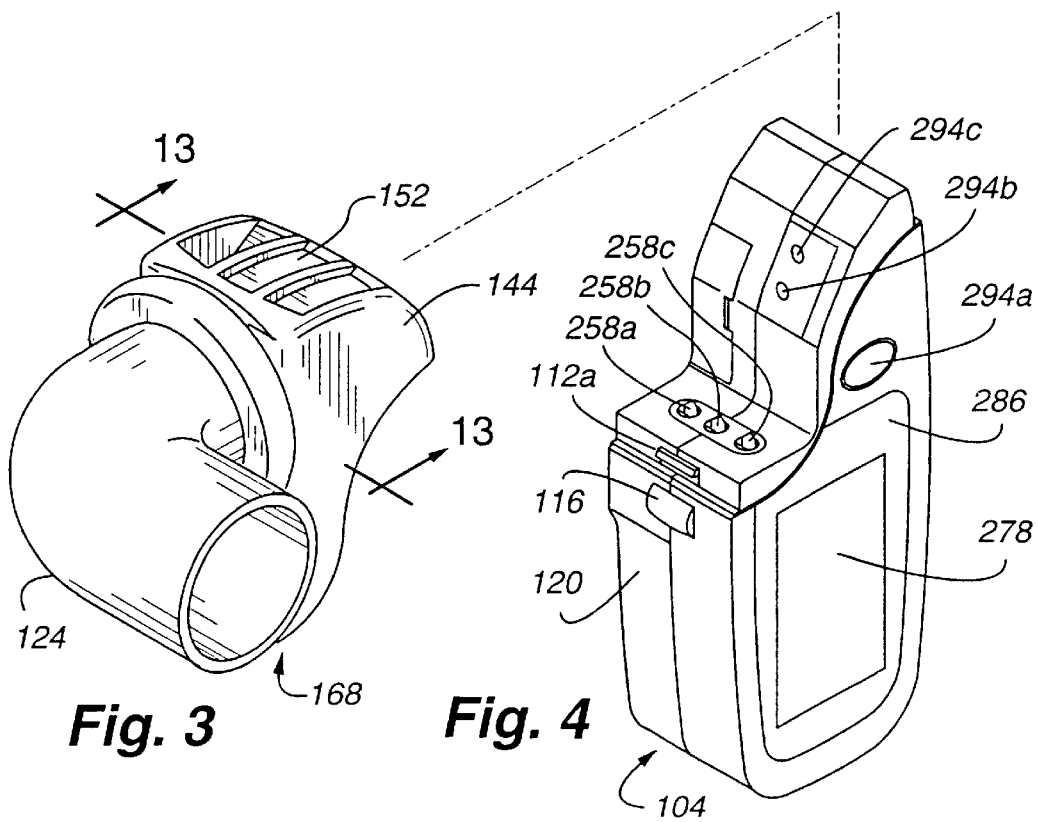
Fig. 3
Fig. 4

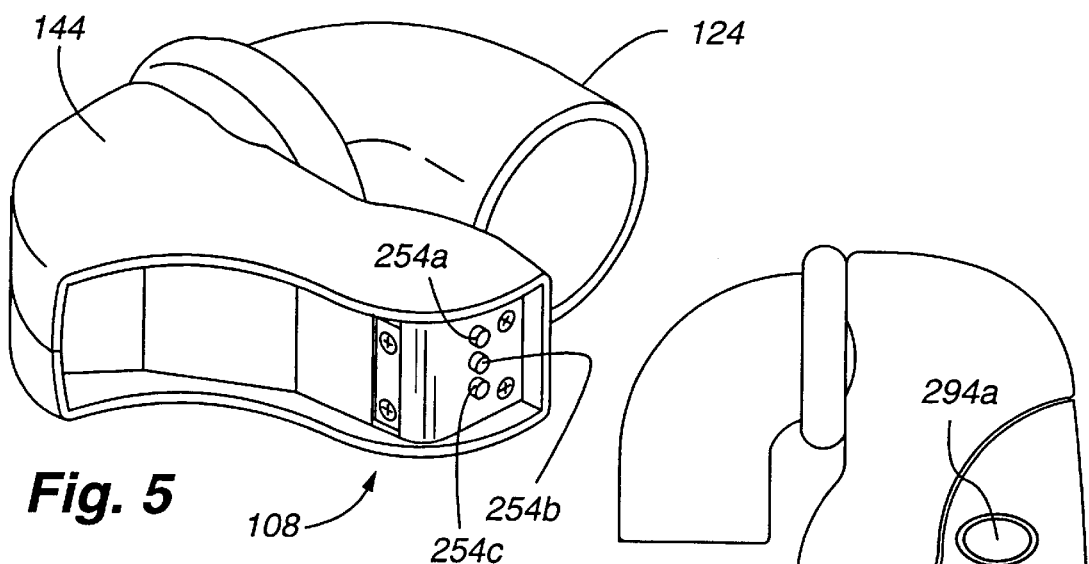
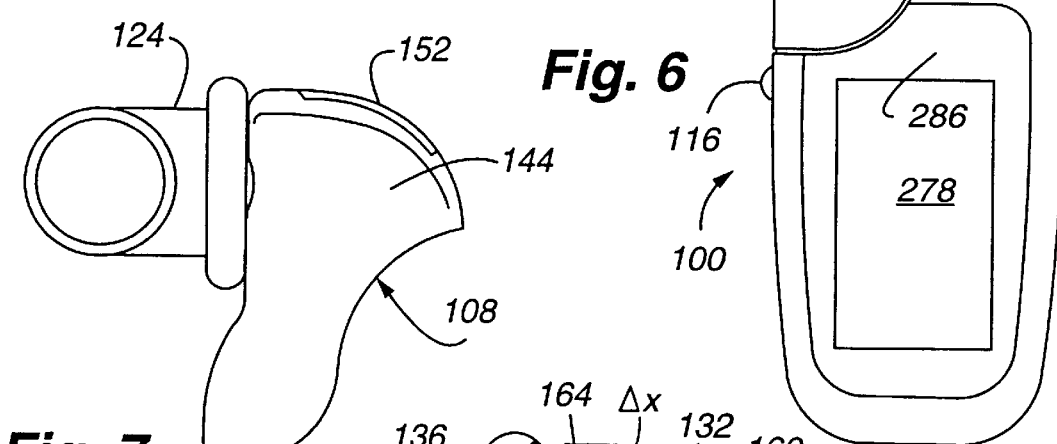
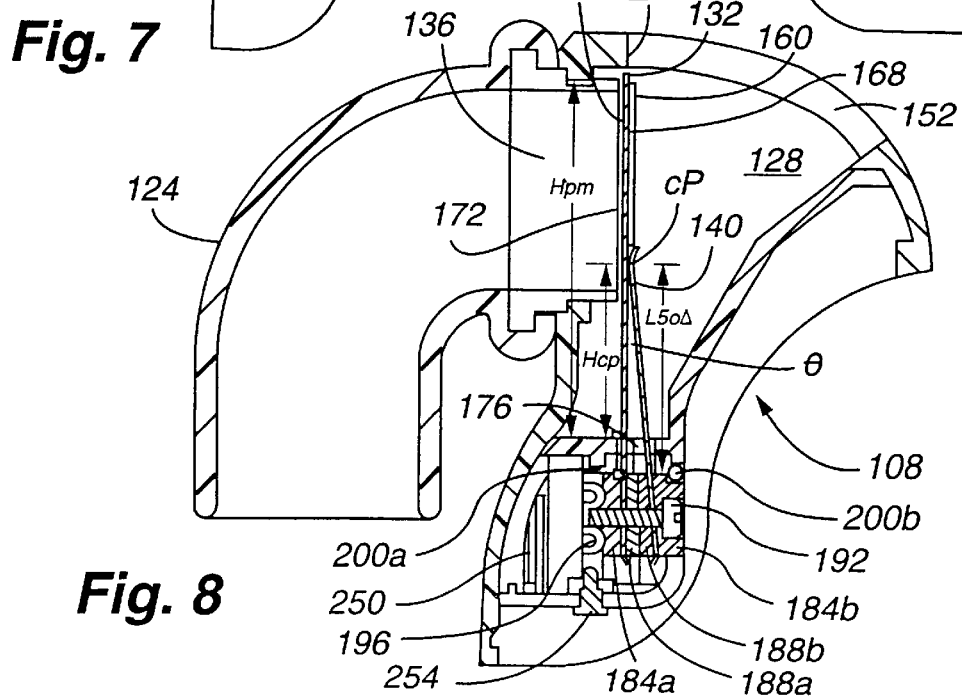

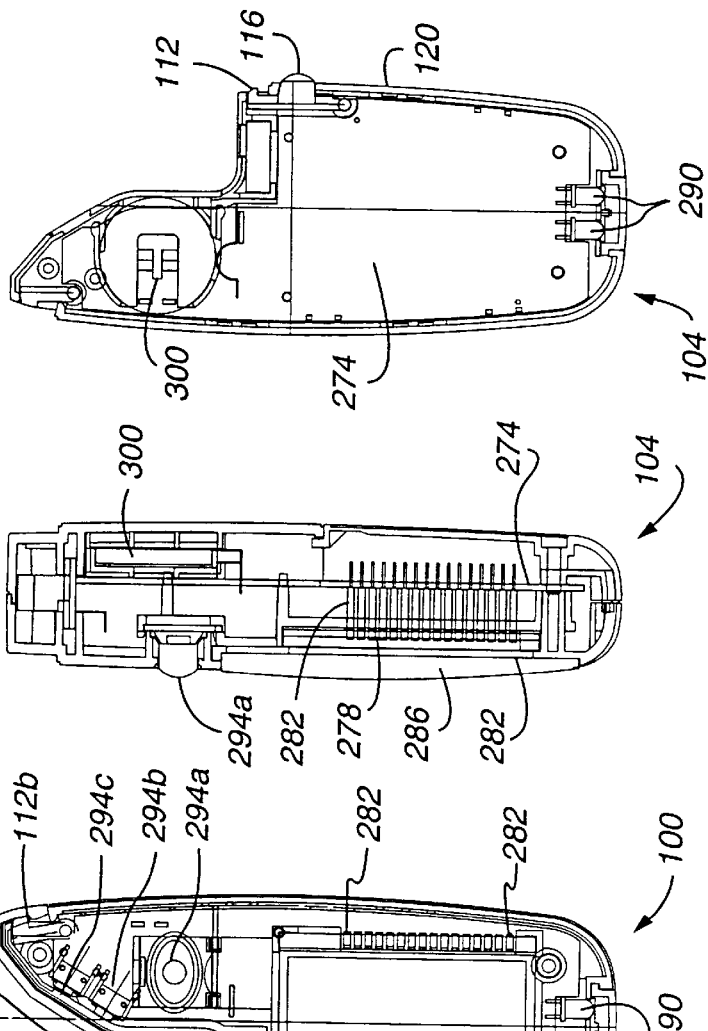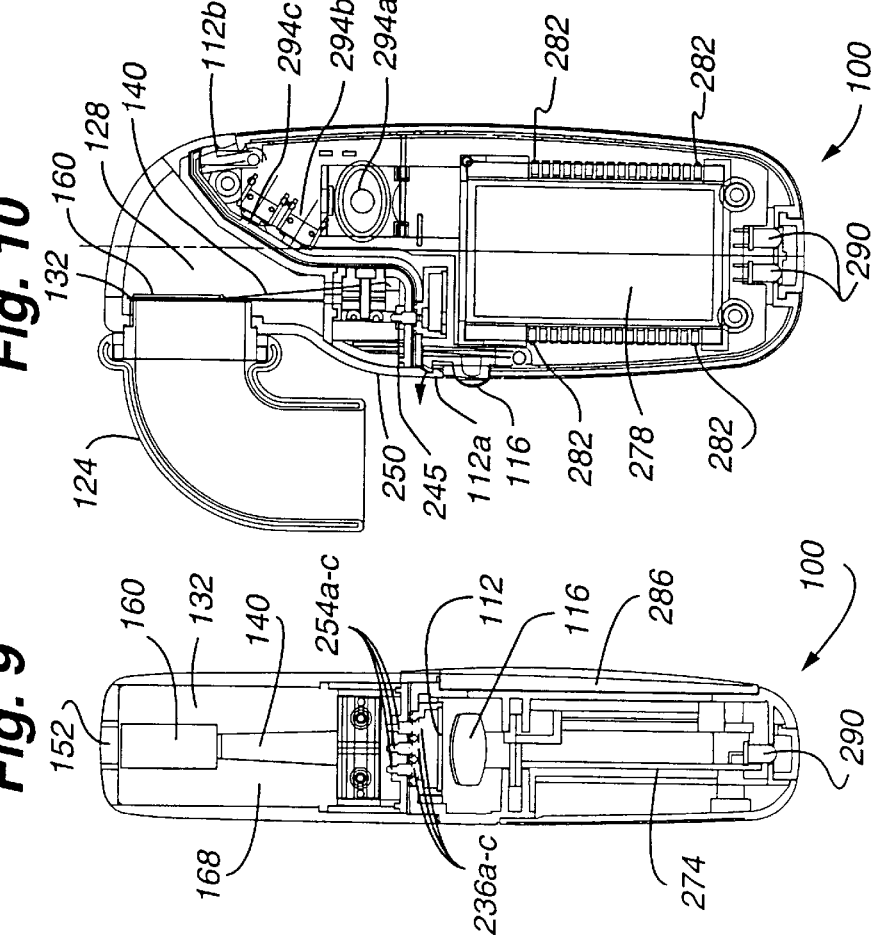

DEVICE AND METHOD FOR MEASURING LUNG PERFORMANCE

FIELD OF THE INVENTION

The present invention relates generally to devices and methods for measuring gas flow parameter(s) and specifically for measuring air flow parameter(s) for diagnosing lung performance.

BACKGROUND OF THE INVENTION

Mechanical and electronic peak flow meters are used to monitor lung performance of patients having respiratory ailments, such as asthma. Mechanical peak flow meters in particular are used by patients to self-monitor lung performance. In such applications, lung performance parameters, such as peak air flow, are periodically recorded in a diary. If lung performance falls below a certain level or if the diary shows a deterioration in lung performance, the patient seeks medical assistance.

Mechanical peak flow meters are typically a spring-loaded device having a peak flow pointer attached to a plate-like spring that is displaced or slid laterally by the exhaled air of the patient to indicate the peak flow rate. Although such devices are inexpensive, the devices provide only a Peak Expiratory Flow Rate (PEFR) measurement and are unable to measure other desirable and important parameters, such as Forced Expiratory Volume in one second ($FEV_1$) (the total volume of air exhaled by the patient over a one second interval) or Forced Expiratory Volume in 6 seconds ($FEV_6$) (the total volume of air exhaled by the patient over a six second interval). The accuracy of such devices is often poor and typically deteriorates over time due. Mechanical devices are also unable to track peak flow measurements by writing the measurements to an electronic memory. The measurements must be manually recorded in the diary.

Electronic devices typically have a fixed or variable orifice and a pressure transducer located on one or both sides of the orifice. A fixed orifice is a reduced diameter passage (which can have any shape) having a fixed cross-sectional area that is independent of air flow rate. A variable orifice is a reduced diameter passage (which can have any shape) having a cross-sectional area that is dependent on air flow rate (e.g., the cross-sectional area increases as the flow rate increases). In either case, the orifice typically causes a back pressure to form in front of the orifice in response to air flow through the orifice. By measuring the back pressure and determining the pressure downstream of the orifice (which is typically ambient pressure), the pressure differential across the orifice can be obtained. The pressure differential permits not only the peak flow to be determined but also $FEV_1$ and $FEV_6$ (when the pressure differential is measured as a function of time). Due to the use of expensive pressure transducers and associated electronics, electronic devices are typically too costly for individual patients in self-monitoring applications. As a result, patients are unable to monitor important lung performance parameters, such as $FEV_1$ or $FEV_6$.

SUMMARY OF THE INVENTION

These and other needs are addressed by the devices and methods of the present invention. The present invention is directed generally to an inexpensive device and method for measuring an (expiratory) air flow parameter, such as PEFR, $FEV_1$, $FEV_6$, Forced Vital Capacity (FVC), and Mid Expiratory Flow Rate (FEF 25-75). The device can be simple to use and portable and/or hand held.

In a first embodiment, a device is provided that includes:

(a) a conduit having an inlet (or mouthpiece) for exhaled air and an outlet (or flow chamber) for the exhaled air;

(b) a plate (or orifice or closure or sensing) member (or vane) movably disposed in the conduit between the inlet and outlet, the plate member at least partially blocking the conduit and moving in response to the passage of the exhaled air through the conduit; and (c) a measuring device for measuring, at a plurality of points in time, at least one of (i) a location of the plate member, (ii) a pressure or force applied by the exhaled air against the plate member, and/or (iii) an air flow parameter (e.g., a rate of volume of flow) and generating a plurality of measurement signals. The plate member is typically shaped such that air flow from the inlet end past the member causes the member to move, e.g., rotatably or linearly, away from a rest or starting position to a succession of other open positions forming an ever widening gap between the member and a part or wall of the conduit or passageway. From the position of the plate member or the force applied to the plate member, the pressure applied to the plate (e.g., the back pressure or the pressure or force applied by the air flow) in front of the plate member can be determined.

In one configuration, the device measures the force applied to the plate by the mass of air contacting the plate (even though there is no back pressure). The force is directly proportional to the flow rate or the kinetic energy of the air flow.

In another configuration, the outlet is at ambient (atmospheric) pressure and therefore the pressure differential across the plate member can be determined. The use of the displacement measuring device thereby eliminates the need for an expensive pressure transducer and related electronics. The device can be designed to comply with the stringent maximum back pressure requirements of the American Thoracic Society (which require the back pressure to be less than about 2.5 cm $H_2O$/liter second measured at 14 liters/second airflow (for monitoring applications)) and 1.5 cm $H_2O$/liter second measured at 14 liters/second airflow (for diagnostic applications)), but also, by selecting the distance between the displacement member and the outlet of the conduit, the relationship between the pressure and air flow for the device can be predetermined (e.g., the shape of the curve when pressure is plotted against flow rate can be controlled). In this manner, extremely low flow rates can be accurately measured.

To permit determination of time dependent parameters, such as $FEV_1$, or $FEV_6$, the device can further include a processing unit for receiving the plurality of measurement signals and an electronic memory, in communication with the processing unit, for recording the location of or pressure or force applied to the plate member at the plurality of points in time. This permits determination of the flow rates at the differing points in time and, therefore, the volumetric flows over a selected time interval. The contents of the electronic memory can be read by the user through a visual display and/or uploaded to a computer to generate an electronic diary for the patient and/or to forward the information by modem to a physician. Physicians can program the device to set goals or targets using a computer (PC) interconnected via a port to the device or keys on the device. In one configuration, the memory is tamper proof, thereby eliminating errors that frequently are associated with manually logged results.

The measuring device can be any suitable device for monitoring the pressure or force applied to the plate member and/or the plate member position as a function of time, such as a strain gauge (e.g., a single, half or full resistor bridge strain gauge), a radiant energy source (e.g., a light or sound energy source) in communication with a radiant energy detector. In one configuration, the device is any type of strain gauge, such as piezoresistive, thin film, semiconductor, and the like, that measures deformation of a plate. A particularly preferred strain gauge has an active circuit and an inactive circuit. By configuring the strain gauge as a half or full resistor bridge, noise as a result of thermal expansion or contraction of the plate member and the like, can be zeroed out. The strain gauge is typically located on an upstream (front) or downstream (rear) surface of the plate member relative to the direction of exhaled air flow.

In another embodiment, a method is provided for determining exhaled air flow. The method includes the steps of:

(a) exhaling air into an inlet of a conduit;

(b) moving a sensing member that is movably disposed in the conduit downstream of the inlet, the sensing member at least partially blocking the conduit and moving in response to the passage of the exhaled air through the conduit; and (c) measuring the location of the sensing member at a plurality of points in time and generating a plurality of location signals. The plurality of location signals can be processed to determine a desired air flow parameter.

In another embodiment, a portable device for measuring respiratory air flow is provided that compensates for the effects of inertia of the plate member. The device includes a self-oscillation dampener (or dampening means) that resists movement of the sensing member. In one configuration, the dampener is located behind and movably (e.g., frictionally) engages the sensing member. The self-oscillation dampener dampens the amplitude of oscillations of the sensing member in response to exhaled air contacting the sensing member. The self-oscillation dampener can also increase the resonant frequency of the sensing member such that the resonant frequency exceeds the frequency of any oscillations imparted to the system by the air flow. In one configuration, the self-oscillation dampener is located on the downstream side of the sensing member. In another configuration, the self-oscillation dampener applies a pressure to the sensing member of no more than about 10 gm or no more than about 10% of the pressure applied to the sensing member by the air flow.

In yet another embodiment, a device for measuring respiratory air flow is provided that includes:

(a) a conduit having an inlet for exhaled air and an outlet for the exhaled air;

(b) a plate member movably disposed in the conduit between the inlet and outlet, the plate member at least partially blocking the conduit and moving in response to the passage of the exhaled air through the conduit; and (c) a measuring device for measuring at least one of a pressure or force applied against the plate member by the exhaled air and generating a measurement signal. The measuring device is located on (e.g., adhered or attached to, etched on, etc.) or otherwise engages the plate member. In a particularly preferred configuration, the measuring device is a strain gauge.

In a further embodiment, a portable device is provided that increases the plate member's resonant frequency for the reasons noted above. The device includes (incorporates) or engages one or more stiffening members to impart rigidity to the plate member without significantly increasing the mass of the member. The stiffening members can be located anywhere on the plate member such as on a peripheral edge(s) of the plate member and/or in the central portion of the plate member. By increasing the rigidity of the plate member, the stiffening members also inhibit or minimize flutter of the member in response to air flow.

In another embodiment, a portable device for measuring respiratory air flow is provided that substantially eliminates the effect of gravity on the air flow measurement. The device includes (a) a conduit having an inlet for exhaled air and an outlet for the exhaled air; and (b) a sensing member for measuring an air flow parameter (e.g., a pressure transducer, a movable plate). The direction of air flow through the inlet is transverse to the direction of air flow at the sensing member. In one configuration, the direction of air flow through the inlet is substantially normal to the direction of air flow at the sensing member. In this design, the positioning of the device when the patient exhales into the conduit has substantially no effect on the air flow measurement. In one configuration, an axis of sensing member movement is substantially normal or orthogonal to an axis of possible movement of the patient during the respiratory test using the device.

In yet a further embodiment, the device includes a detachable or removable head assembly that includes the input conduit, sensing member and outlet conduit. The head assembly is removable for cleaning. In this manner, the device does not require a bacterial filter.

The above-described embodiments and configurations are neither complete nor exhaustive. As will be appreciated, other embodiments of the invention are possible utilizing, alone or in combination, one or more of the features set forth above or described in detail below.

BRIEF DESCRIPTION OF THE DRAWINGS

FIG. 1 is perspective view of a user operating the peak flow meter according to one embodiment of the present invention;

FIG. 2 is a perspective view of the flow meter with the inlet in the undeployed position;

FIG. 3 is a perspective view of the head assembly disengaged or detached from the body of the flow meter;

FIG. 4 is a perspective view of the body of the flow meter with the head assembly detached;

FIG. 5 is a bottom view of the detached head assembly;

FIG. 6 is a side view of the flow meter with the inlet in the undeployed position;

FIG. 7 is a side view of the detached head assembly with the inlet in the deployed position;

FIG. 8 is a cross-sectional view along line 8—8 of FIG. 2;

FIG. 9 is an end view depicting the flow meter with a portion of the housing removed to reveal the flow meter interior;

FIG. 10 is a side view depicting the interior of the flow meter with a portion of the housing removed to reveal the flow meter interior;

FIG. 11 is an end view (opposite the end view of FIG. 9) depicting the flow meter with a portion of the housing removed to reveal the flow meter interior;

FIG. 12 is a side view (opposite the side view of FIG. 10) depicting the flow meter with a portion of the housing removed to reveal the flow meter interior;

DETAILED DESCRIPTION

Figure 13:
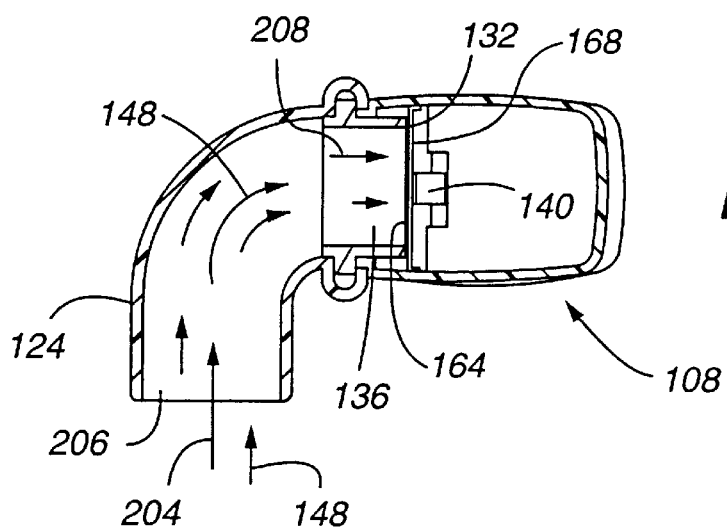
FIG. 13 is a cross-sectional view taken along line 13—13 of FIG. 3.

FIGS. 1–12 depict a peak flow meter 100 according to one embodiment of the present invention. The flow meter 100 includes a body assembly 104 and a detachable head assembly 108. Referring to FIG. 4, the head assembly 108 can be detached from the body assembly 104 by means of a front latch 112a activated by pressing a release button 116 located on the front 120 of the body assembly 104. Rear latch 112b is not activated by the release button but simply holds the rear of the head assembly.

Referring to FIGS. 4 and 9–12, the body assembly 104 generally includes signal processing circuitry, a processor, and a display, all enclosed within a body housing. The body housing is typically formed from a lightweight rigid material such as plastic.

Referring to FIGS. 3, 5, 8–10, and 16, the head assembly 108 generally includes a rotatable (or adjustable) inlet conduit 124, an outlet conduit 128, a plate member 132 adjacent to an orifice 136, and a self-oscillation dampener 140 engaging the plate member 132, all enclosed by a head housing 144 that is typically formed from the same material as the body housing.

Figure 14:
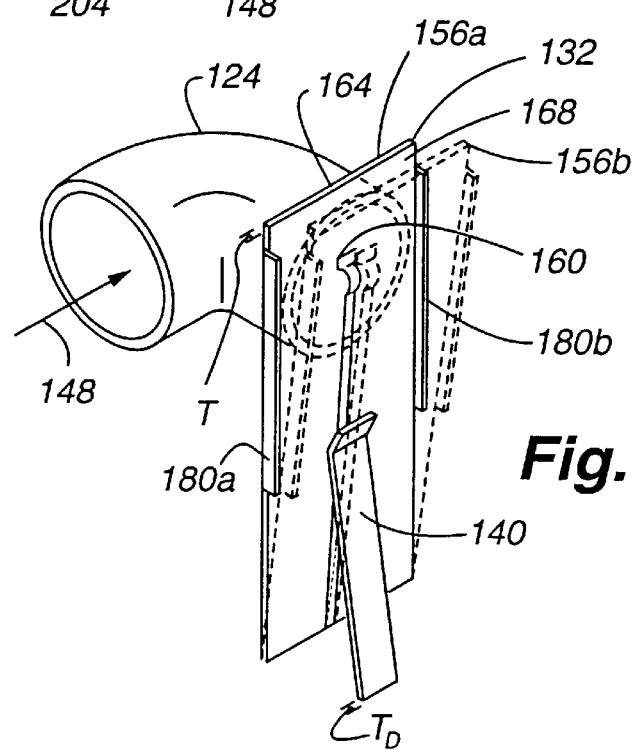
FIG. 14 is a schematic view of the inlet and plate member in various positions.
Figure 15:
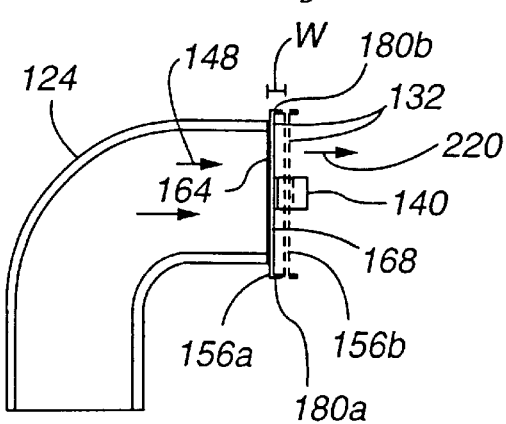
FIG. 15 is a top view of the schematic view of FIG. 14.
Figure 16:
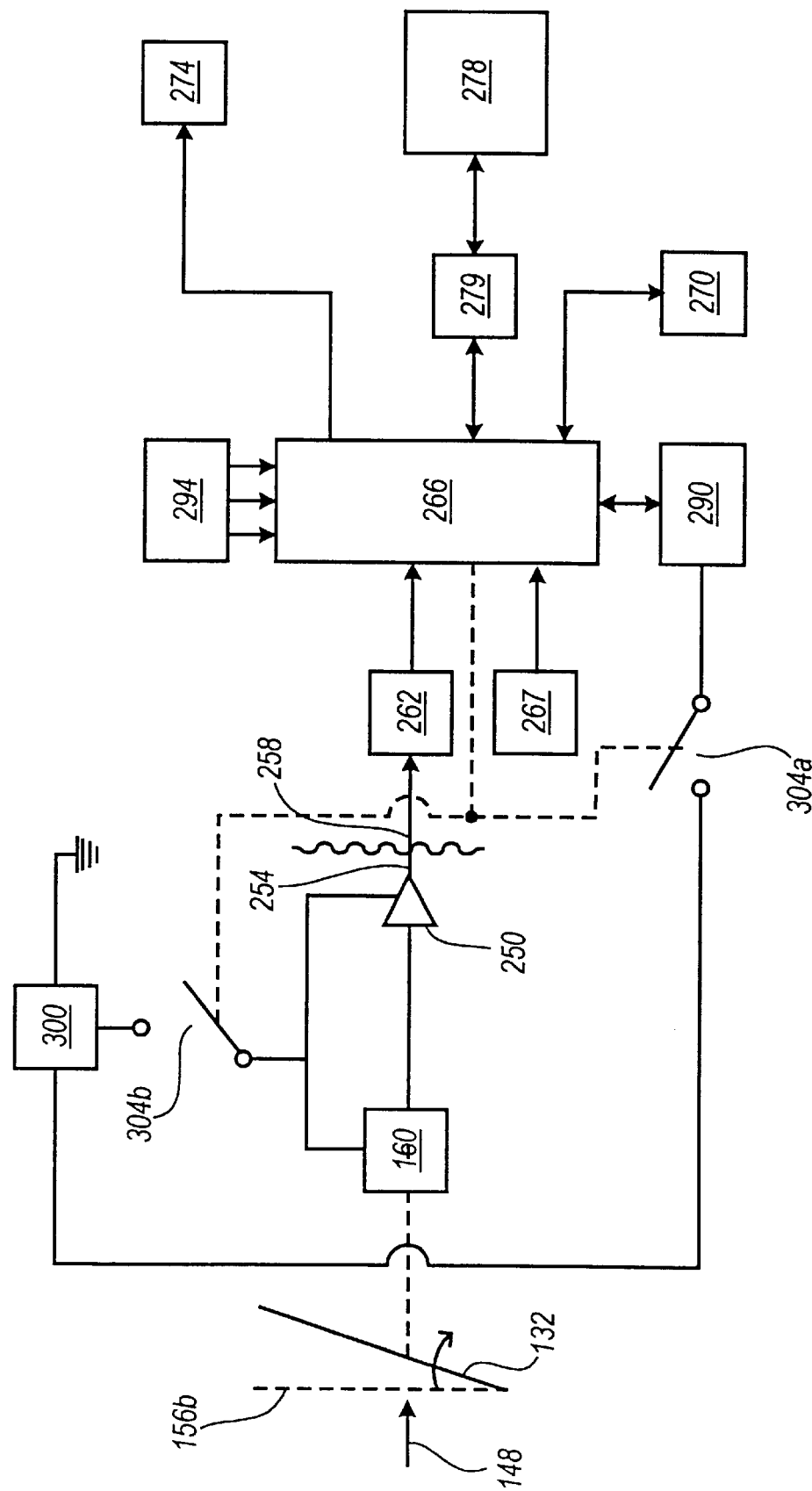
FIG. 16 is an electrical flow schematic of the peakflow meter.

Referring to FIGS. 14 and 15, the plate member 132 is movably or rotatably engaged with the head housing 144 to permit exhaled air 148 passing through the inlet conduit 124 and the orifice 136 to displace the plate member 132 away from the orifice 136. When the plate member 132 is displaced away from the orifice 136, the exhaled air 148 can pass into the outlet conduit or flow chamber 128 and through the outlet or exhaust 152 into the exterior environment. The clearance between the bent edges of the plate member and the adjacent interior surfaces of the head housing is typically low (e.g., no more than about 0.5 mm to improve measurement accuracy.

As the plate member 132 is displaced from a starting position 156a to a new position 156b (FIGS. 14 and 15), a strain gauge 160 located on or etched onto the plate member 132 generates an electrical signal that may be processed by known techniques to determine the force applied to the plate member 132 by the air 148 flowing through the inlet conduit 124. As will be appreciated, the electrical signal will vary as the length of the resistor in the strain gauge varies in response to deformation of the plate member 132. If the strain gauge 160 were to be located on the front surface 164 of the plate member 132, the resistor length increases as the plate member 132 is displaced. If the strain gauge 160 is located on the rear surface 168 of the plate member 132, the resistor length decreases as the plate member 132 is displaced. As discussed below, the electrical signal can be used to determine directly the pressure or force applied to the plate member by the air flow as a function of time and the resulting waveform integrated over the appropriate time interval to provide $FEV_1$ or $FEV_6$.

Figure 18A:
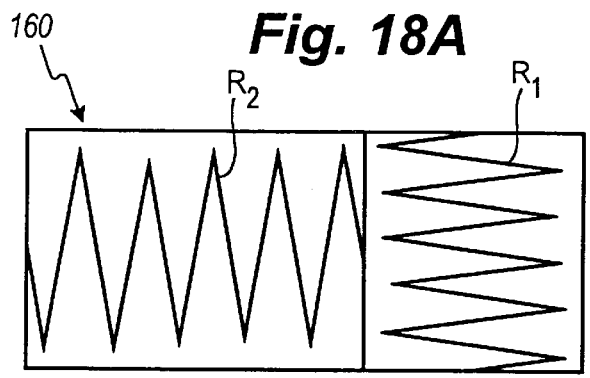
FIGS. 18A and B are respectively a configuration of a resistor bridge for the measuring device and an electrical flow schematic of the device.
Figure 18B:
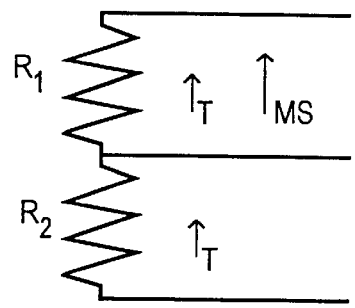

FIGS. 18A and B depict a configuration of a strain gauge 160 that is particularly useful in many applications. The strain gauge 160 is a full resistor bridge design having resistors $R_1$ and $R_2$. The resistor $R_1$ is orthogonally oriented to the resistor $R_2$ to permit background variations or noise (signal "T") in the electrical signal due to thermal effects to be zeroed out. In other words, the resistors $R_1$ and $R_2$ are electrically connected in parallel such that changes in the length of each resistor due to thermal expansion and contraction of the plate member 321 eliminate one another (because the plate member 132 will uniformly expand or contract in all directions). When the plate member 132 is displaced by the air flow through the inlet conduit 124, the length of the resistor $R_2$ will remain substantially constant while the length of resistor $R_1$ will vary to generate, signal "MS" measurement.

The strain gauge 160 can be adhered or otherwise attached to the plate member 132 or etched into the plate member 132 (which is typically of metal construction) by known techniques. Typically, the strain gauge will be fabricated separately and later attached to the plate member 132 for reasons of cost.

Referring to FIG. 8, the distance Δx between the upstream or front surface 164 of the plate member 132 and the plane of the orifice outlet 172 (when the plate member is at its starting position 156a (FIG. 14)) (i.e., when no air is flowing through the inlet conduit 124)) can determine the linearity and sensitivity of the response of the system to the air flow through the inlet conduit 124. For example, if Δx were zero an extremely high gain (or extreme sensitivity at low flow rates) would be realized when the air flow 148 first contacts the plate member. However, the accuracy of the measurement would decrease rapidly as the flow rate increases. As Δx becomes larger, the opposite effect occurs. Although a more linear response is realized at higher Δx's, the system would have a very low sensitivity at low flow rates. Preferably, Δx is no more than about 5 mm and more preferably ranges from about 0 to about 2.5 mm.

The plate member 132 can be composed of any preferably lightweight, noncorrosive, high strength, substantially rigid or rigid material, with metal, such as any 3XX stainless steel alloy 15-5, 15-7, 17-4, and 17-7 which are sold by major suppliers, being more preferred.

It is important to reduce the mass of the plate member 132 to reduce the impact of gravity on the displacement of the plate member 132 by air flow 148 and reduce the severity (frequency and amplitude) of plate member oscillations. If the plate member 132 is too thin, flutter of the plate member 132 can adversely impact the accuracy of the measurement. Preferably, the plate member 132 has a thickness "T" (FIG. 14) ranging from about 0.05 to about 0.5 mm and more preferably from about 0.05 to about 0.25 mm. Typically, the weight of the plate member 132 is no more than about 0.6 gms and more typically ranges from about 0.3 to about 2 gms.

To absorb energy imparted to the plate member 132 by the air flow 148 (and thereby reduce the magnitude of oscillations of the plate member 132), the self-oscillation dampener 140 resists (typically frictionally) displacement of the plate member 132. As will be appreciated, oscillations can cause a loss of measurement accuracy, especially at the peaks, which translates into an inaccurate computation of the desired respiratory parameter(s).

Referring to FIG. 8, a number of design parameters for the self-oscillation dampener 140 are depicted. Typically, the contact angle θ ranges from about 0 to about 75° and more typically ranges from about 15 to about 65°. The height $H_{CP}$ of the contact point "CP" between the dampener 140 and plate member 148 typically ranges from about 25 to about 95% of the height $H_{PM}$ of the plate member 132 above the same datum plane. The length "$L_{SOD}$" of the dampener 140 from the contact point to the datum plane typically ranges from about 10 to about 150% of the height $H_{PM}$ of the plate member 132. As will be appreciated, the datum plane is the plane containing the rotational axes for the plate member 132 and dampener 140. The plate member 132 and dampener 140 pass through a common hole 176 to allow freedom of rotation. The dampener 140 typically has a thickness "$T_0$" (FIG. 15) ranging from about 0.05 to about 1 mm and is fabricated of a metal such as the stainless steel alloy referred to above. Typically, the self-oscillation dampener 140 applies a pressure to the plate member 132 of no more than about 10 gm and more preferably ranging from about 2.5 to about 8 gm or no more than about 10% and more typically no more than about 1 to about 7.5% of the pressure applied to the front surface 164 plate member 132 by the air flow 148.

The plate member 132 is preferably designed such that the natural or self-resonant frequency of the plate member 132 is higher than than the frequency of the oscillations that are imparted to the plate member 132 by the air flow 148. Typically, the plate member 132 is designed to provide a natural frequency of the plate member 132 that is at least about 70 Hz and more typically at least about 75 Hz based on the assumption that the air flow 148 will impart a maximum frequency of 25 Hz to the plate member 132. In this manner, measurement inaccuracies caused by oscillation of the plate member 132 are maintained at acceptable levels.

To provide such a high natural frequency and to significantly reduce flutter of the plate member 132, the plate member 132 can have one or more stiffening members 180a,b, (FIG. 14). The stiffening members can be in any shape and any location on the plate member 132 and can be integral with the plate member 132 or nonintegral with and attached in some manner to the plate member 132. The width "W" (FIG. 15) of the stiffening members 180a,b typically ranges from about 0.1 to about 1.0 mm and are typically formed as an integral part of the plate member 132.

FIG. 8 depicts the various interconnected components supporting the plate member 132 and the self-oscillation dampener 140. The components include inner and outer parts 184a,b (which are preferably a lightweight material such as plastic) and inner components 188a,b (which are preferably a high strength material such as a metal (e.g., a stainless steel). A fastener, such as a screw 192 and washer or nut 196, are used to fasten the various components together. A sealant 200a,b, such as a silicon sealant, is positioned to block moisture from penetrating into the interior of the head assembly 108 and damaging electrical components contained therein. The various parts of the head housing in the head assembly 108 are attached together by a suitable technique to provide protection from moisture. A particularly preferred technique is ultrasonic welding.

To substantially eliminate the effects of gravity on the air flow measurement, the inlet conduit 124 provides a change in the direction of air flow 148 upstream of the plate member 132. Referring to FIG. 13, the input direction 204 of air flow through the inlet 206 is transverse (typically orthogonal) to the direction 208 of the air flow 148 at the outlet of the orifice 136. As can be seen from FIG. 1, the positioning of the meter 100 when the patient exhales into the inlet has substantially no effect on the air flow measurement. Stated another way, the direction 220 of plate movement (FIG. 15) is substantially normal or orthogonal to a direction 224 (FIG. 1) of possible movement of the user during the respiratory test. As shown in FIG. 13, this result is accomplished by making the air flow direction 204 at the inlet 206 substantially orthogonal to the air flow direction 208 at the orifice 136 and making the air flow direction 208 substantially normal to the plane of the front surface 156a of the plate member 132.

For the convenience of the user, the inlet conduit 124 can be rotated freely between an undeployed position (FIG. 2) for ease of handling and the deployed position (FIG. 7).

The electronics of the meter will now be discussed with reference to FIGS. 4–5, 8–12, and 16. The signal from the measurement device 160 is received by an amplifier (which typically has a gain of about 1000) (and in some cases a filter) 250, amplified (and in some cases filtered to remove noise) and transmitted via three contacts 254a–c and 158a–c from the head assembly 108 to an analog-to-digital converter 262. The signal is converted from analog to digital by the converter 262 and processed as set forth below with reference to FIG. 17 by a microprocessor 266. The microprocessor 266 accesses a nonvolatile memory 270, such as an Electrically Erasable Programmable Read-Only Memory or EEPROM. The memory can store a variety of information including calibration and operating information. This information can be programmed into the chip at the time of manufacturing.

The microprocessor 266 is typically connected to various components. In one embodiment for example, the microprocessor 266 is connected to an audio device 274, such as a buzzer, to provide a warning signal such as when the air flow rate and/or volume is below a predetermined level. The microprocessor is connected to a system clock 267 for timing information. The clock can access nonvolatile memory 270 to protect data and information. The microprocessor is connected to a display module 278, such as a Liquid Crystal Display or LCD or a number of Light-Emitting Diodes or LEDs, via a plurality of contacts 282 located on either side of the display. The microprocessor is connected to a display drive 279 for the display module 278. In one configuration, the display is a segment-type display. The display is covered by lens 286. The microprocessor is connected to an Infrared Communication or IR ports 290 to upload information from the memory 270 to a peripheral computing device, such as a PC (not shown). The microprocessor is connected to a plurality of keys 294*a–b*. The keys are incorporated into the display module. The keys are hereinafter referred to as the operator key 294*a*, the scroll key 294*b*, and the settings or select key 294*c*.

A common printed circuit 274 board typically contains the analog-to-digital converter 262, microprocessor 266, memory 270, display drive 279, and system clock 267. The PCB is located in the body assembly 104.

A power source 300, which is typically a small sized battery such as a 2032 lithium cell having a power capacity of 3 Volts, powers the various electrical components.

Switches 304*a,b* activate and deactivate the various components. Switches 304*a,b* are activated by the microprocessor 266 as described below.

Figure 17A:
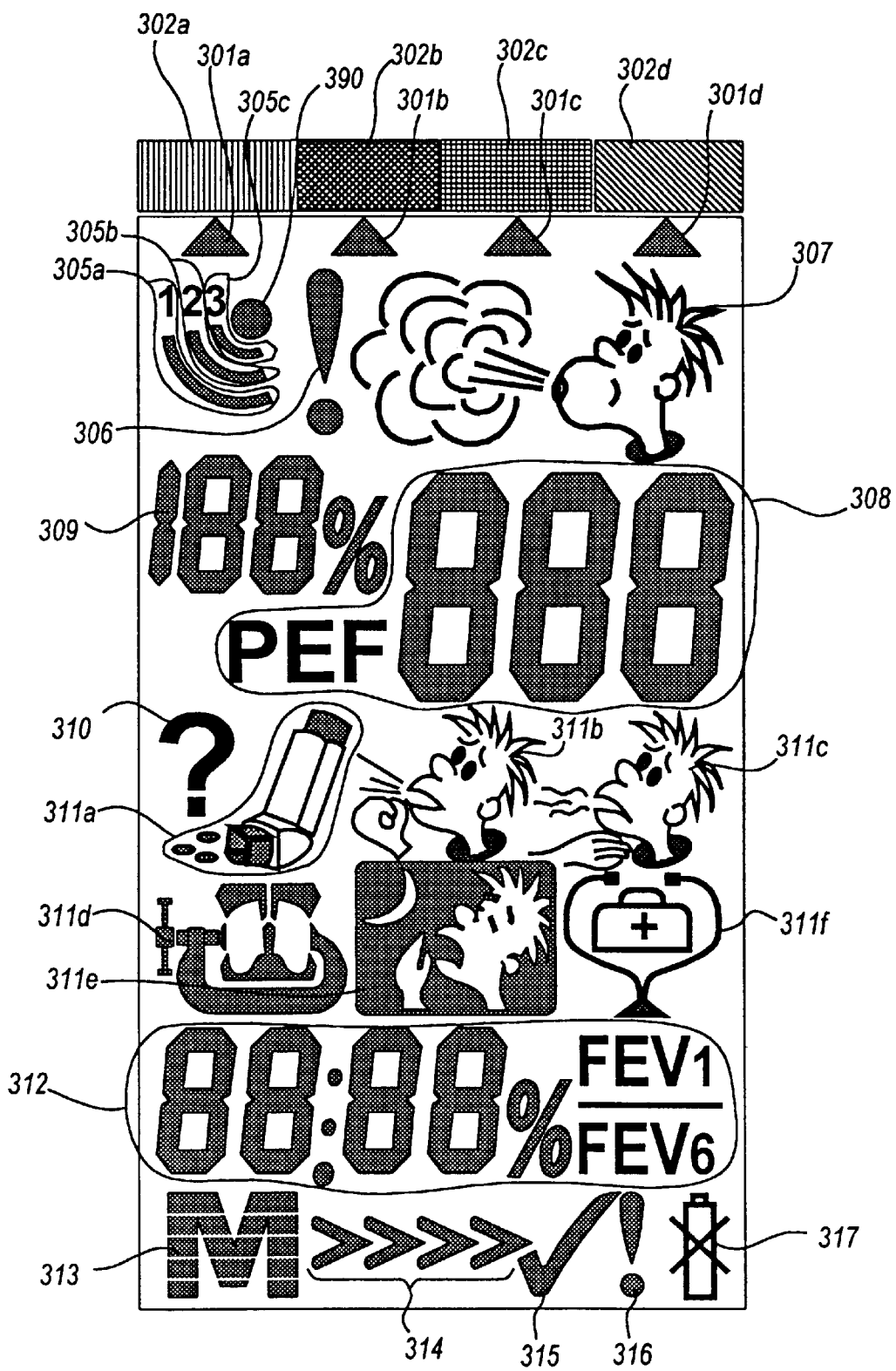
FIG. 17A is a plan view of the segmented display.

The display module 278 is depicted in FIG. 17A. Each of the segment indicators 301*a–d* correspond to a zone indicator 302*a* (red zone), 302*b* (orange zone), 392*c* (yellow zone), and 302*d* (green zone). The segment indicators 301*a–d* are activated to indicate which of the colored zones a PEF reading corresponds to. Alarm segment 303 includes three subsegments 305*a–c*, each of which corresponds to a separate alarm setting. When an alarm is triggered, the corresponding subsegment 305*a–c* and center 390 is illuminated along with the exclamation mark segment 306. The blow segment 307 is illuminated when a blow test is to be initiated. The PEF segment 308 is activated to display the results of a blow test. The reference segment 309 is illuminated to display the percent of the reference PEF to which the PEF measured for the blow test corresponds. The question segment 310 is activated during the symptom score mode when the microprocessor is scrolling through diary questions. The question segments 311*a–f* correspond to medication frequency (inhaler segment 311*a*); coughing severity (cough segment 311*b*); wheezing severity (wheeze segment 311*c*); chest tightening rating (chest clamp segment 311*d*); existence of nocturnal awakenings (True/False) (yawning segment 311*e*); and supplemental questions (medical bag segment 311*f*). The lower display 312 is used to display the time, $FEV_1$, $FEV_6$, and the ratio of $FEV_1$:$FEV_6$. The M segment 313 is illuminated to indicate a full memory 270. The transfer segment 314 is illuminated during the uploading or downloading of information. The check segment 315 is illuminated upon successful completion of the transfer. The lower exclamation segment 316 is illuminated upon unsuccessful completion of the transfer. Finally, the low battery segment 317 is illuminated when the power level falls below a predetermined level.

Figure 17B:
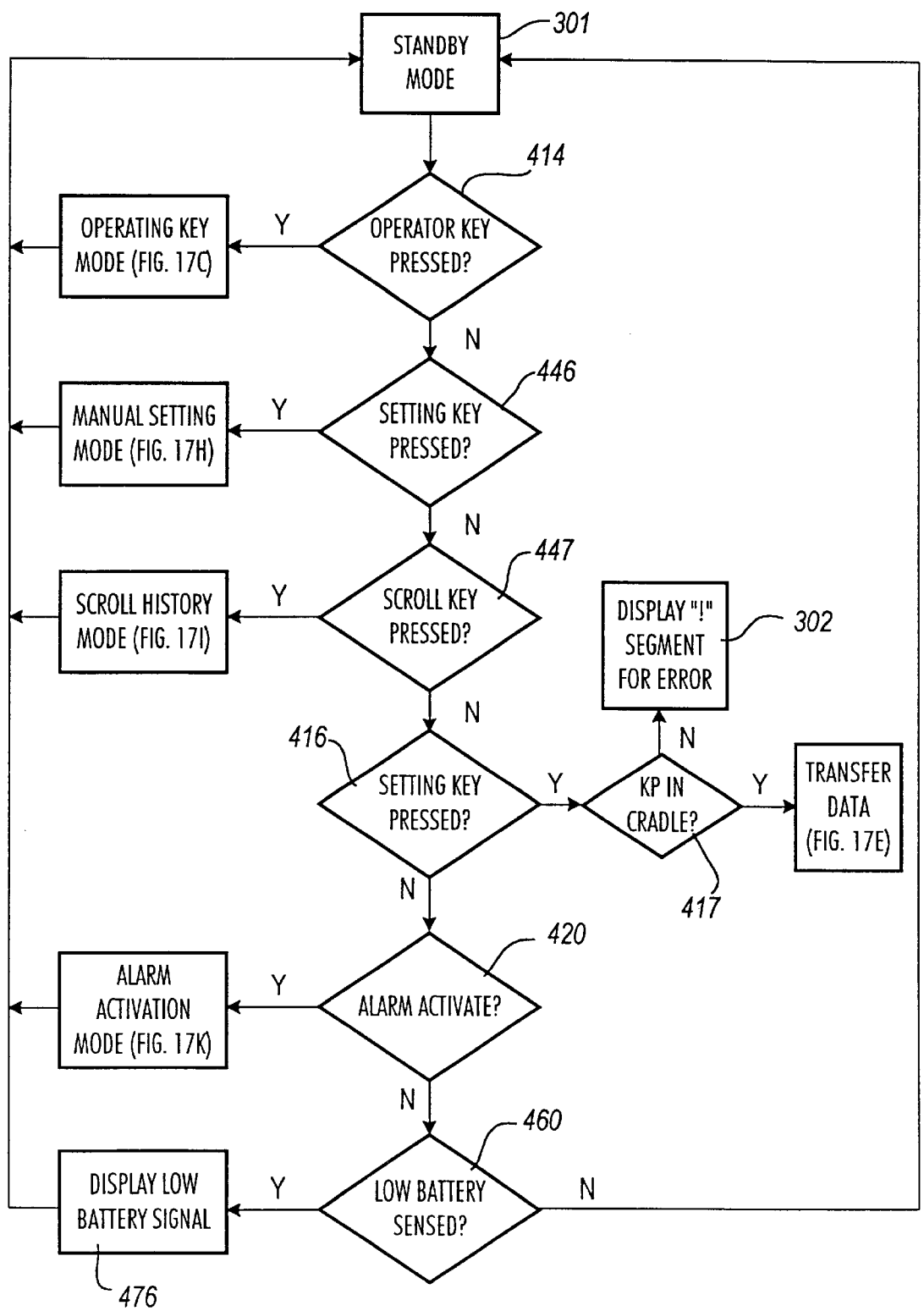
FIGS. 17B–K are flow charts of the software for operating the meter.

Referring to FIGS. 17A–K, the operation of the device will now be described. Referring to FIG. 17B, the device is typically in the standby mode 301. In the standby mode, the microprocessor deactivates the switches 304*a,b* to conserve power and awaits instructions from the user.

Figure 17C:
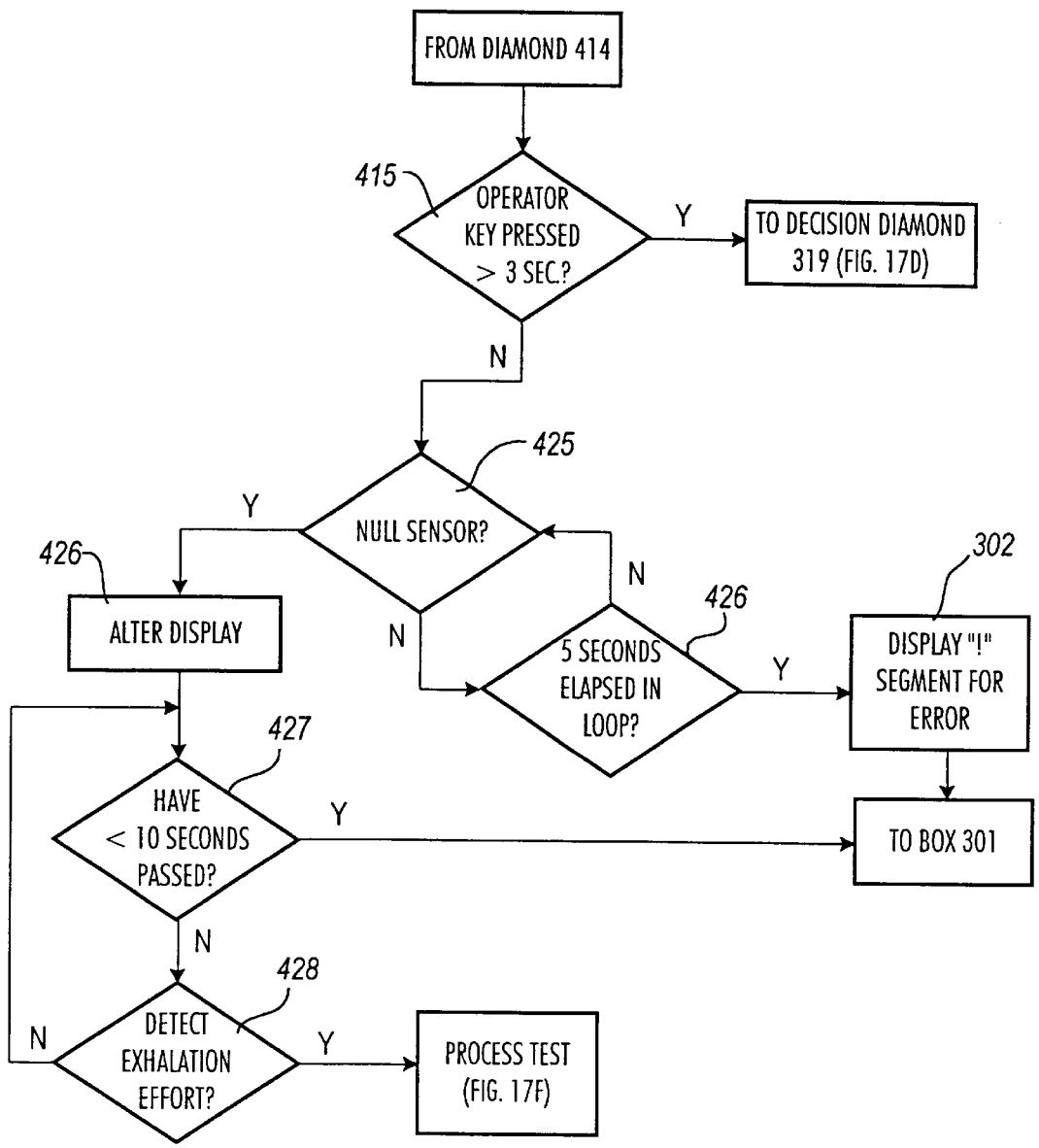

If the operator key is pressed (see decision diamond 414), the microprocessor enters into the operating key mode or subroutine which is depicted in FIG. 17C. Referring to FIG. 17C, the microprocessor determines in decision diamond 415 whether the operator key 194 was pressed and held down for more than three seconds. If so, the microprocessor proceeds to decision diamond 319 in FIG. 17D.

Figure 17D:
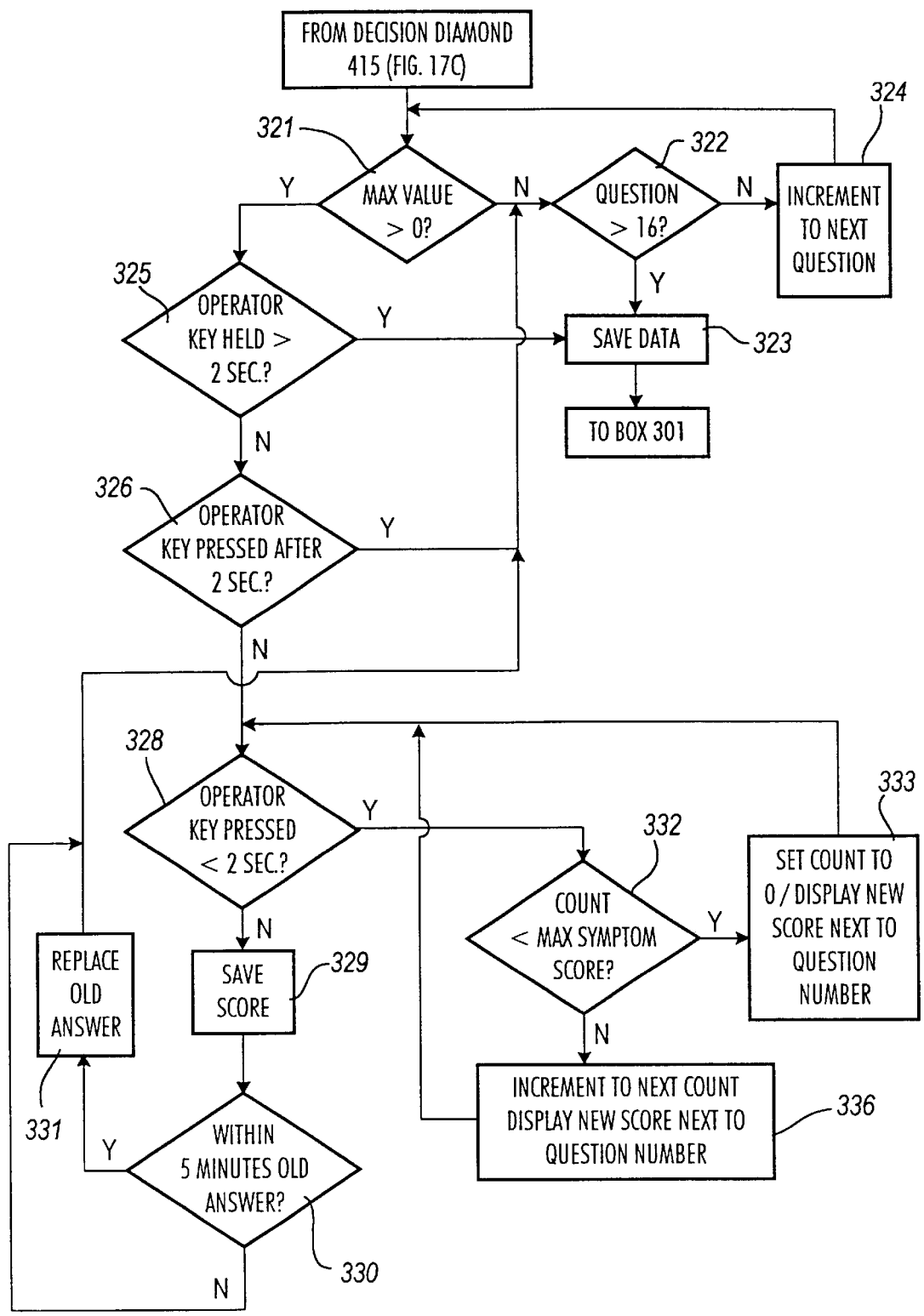

In FIG. 17D, the device is in the symptom score mode or subroutine in which the user can create and/or revise the diary. Referring to FIG. 17D, the microprocessor determines whether a symptom score is going to be entered by waiting for a keystroke within ten seconds. If so, the microprocessor proceeds to decision diamond 321. If the system score is zero (meaning that the question is disabled), the microprocessor proceeds to decision diamond 322. In decision diamond 322, the microprocessor determines if the question number is more than sixteen (the maximum number of diary questions). If so, the microprocessor in box 323 saves the entered system scores. If not, the microprocessor in box 324 increments to the next question and returns to decision diamond 321. If the maximum value in decision diamond 321 exceeds zero, the microprocessor determines in decision diamond 325 if the operator key 294*a* was held down by the user for more than 2 seconds. If so, the microprocessor proceeds to box 323. If not, the microprocessor proceeds to decision diamond 326 where the microprocessor determines if the operator key 294*a* was pressed down again after the 2 second interval of decision diamond 325 (i.e., the user is incrementing the symptom score). If so, the microprocessor proceeds to box 322. If not, the microprocessor proceeds to decision diamond 328 where the microprocessor determines if the operator key was pressed within two seconds of the last pressing of a button or key. If not, the microprocessor saves the symptom score in box 329 and proceeds to decision diamond 330 where the microprocessor determines if the symptom score was entered within 5 minutes of a former symptom score for the same question. If not, the microprocessor returns to decision diamond 322. If so, the microprocessor replaces the old symptom score in box 331 and then proceeds to decision diamond 322. Returning again to decision diamond 328, if the operator key 294*a* was pressed within 2 seconds of the pressing of the previous key, the microprocessor proceeds to decision diamond 332. In decision diamond 322, the microprocessor determines if the entered symptom score exceeds the maximum symptom score. If so, the microprocessor in box 333 sets the entered symptom score to zero and displays the new score in segment 312 (to the right of the colon) next to the question number (to the left of the colon) and returns to decision diamond 328. If not, the microprocessor in box 336 increments to the next count or symptom score and displays the new score in segment 312 and the question number in segment 310 and returns to decision diamond 328.

Returning to FIG. 17C if the operator key 194*a* is held down for less than three seconds, the microprocessor proceeds to decision diamond 425. If the operator key 194*a* is pressed again while the microprocessor is in the loop of FIG. 17C, the microprocessor returns to decision diamond 425. Alternatively, if 10 seconds elapse between the pressing of keys, the microprocessor returns to the standby mode 301.

In decision diamond 425, the microprocessor determines if the sensor is successfully nulled. In this operation, the microprocessor beeps; activates switches 304*a,b;* delays for a specified period without reading the analog-to-digital input to allow the DC supply to the operating amplifier to stabilize; and checks for a valid sensor signal. A valid signal is typically analog-to-digital counts in the range of 60 mv to 140 mv. If a valid signal is not detected, the microprocessor proceeds to decision diamond 426 where it determines whether five seconds has passed. If not, the microprocessor loops back to decision diamond 425. If five seconds has passed, the microprocessor activates segment 306 to display "!" and returns to the standby mode 301. Returning to decision diamond 425, if the sensor is nulled successfully the microprocessor averages the last sixteen counts from the analog-to-digital converter 262 and stores them as the absolute zero baseline. The microprocessor in box 426 activates segment 307 and zeros out segments 308, 309 and 312 and provides an audible pattern tone for test initiation. In decision diamond 427 if more than ten seconds has elapsed, the microprocessor returns to the standby mode 301. If less than ten seconds has elapsed, the microprocessor in decision diamond 428 determines whether an exhalation effort is detected. If not, the microprocessor loops back to decision diamond 427. If so, the microprocessor proceeds to box 429 (FIG. 17F) and collects data. When the flow signal exceeds the absolute zero baseline by at least 30 counts, segment 307 is deactivated and the time is marked as "TIME ZERO". The data is collected to memory 270 beginning with the "TIME ZERO" data point. In box 430, the data is processed by computing the back extrapolation time point, the 80 millisecond peak flow or PEF80, the uncorrected $FEV_1$ and $FEV_6$, the back extrapolation volume (BEV), and finally the corrected PEF80, $FEV_1$, and $FEV_6$. The correction can be performed using any known mathematical corrective techniques and empirical data to correct for one or more respiratory, environmental, or other parameters, as will be obvious to those skilled in the art.

In decision diamond 431 the microprocessor determines if a cough occurred during the test. This is determined by analyzing the change in flow between adjacent samples from PEF to the first second (first 100 samples). If the change is above a predetermined level (typically greater than about 50% of the flow of the previous sample) a cough is assumed to have occurred. If not, the microprocessor in decision diamond 432 determines if the time interval for $FEV_1$ is less than one second. If not, the microprocessor determines in decision diamond 433 if there is a back extrapolation error. Such an error is deemed to exist when the back extrapolation (BE) error is equal to or greater than 0.15 Liters. If not, the microprocessor in decision diamond 434 whether the PEF is less than 30% or more than 150% of the reference PEF. If any of the queries for decision diamonds 432, 433, and 434 are true, the microprocessor in box 435 activates segment 306 to indicate an error. After performing box 435 or if the query in decision diamond 434 is false, the microprocessor proceeds to decision diamond 436 and determines if the previous test was done within five minutes. If so in box 437, the parameters are replaced in memory 270 with the new test results, if no error is identified. If not, the new test results in box 438 are saved to memory 270.

The results are displayed in box 439 for the user after the test. As will be appreciated, the following results are displayed before the test: (a) the PEF80 result of the previous test in segment 308; (b) the percent reference PEF in segment 309; and (c) the zone indicator 301a–d corresponding to the percent reference PEF. After the test is completed, the new values for these variables are displayed along with the values for $FEV_1$ and the FEV1 symbol in segment 312. After three seconds or when the operator key 194a is pressed, the display is changed by replacing the $FEV_1$ value for the $FEV_6$ value and the FEV1 symbol for the FEV6 symbol in segment 312. After three more seconds or when the operator key 194a is again pressed, the display is changed by replacing the $FEV_6$ value with the $FEV_1/FEV_6$ value and the FEV6 symbol for the FEV1/FEV6 symbol 312. After three more seconds these steps are repeated in the sequence described and the microprocessor then proceeds to standby mode 301.

Figure 17E:
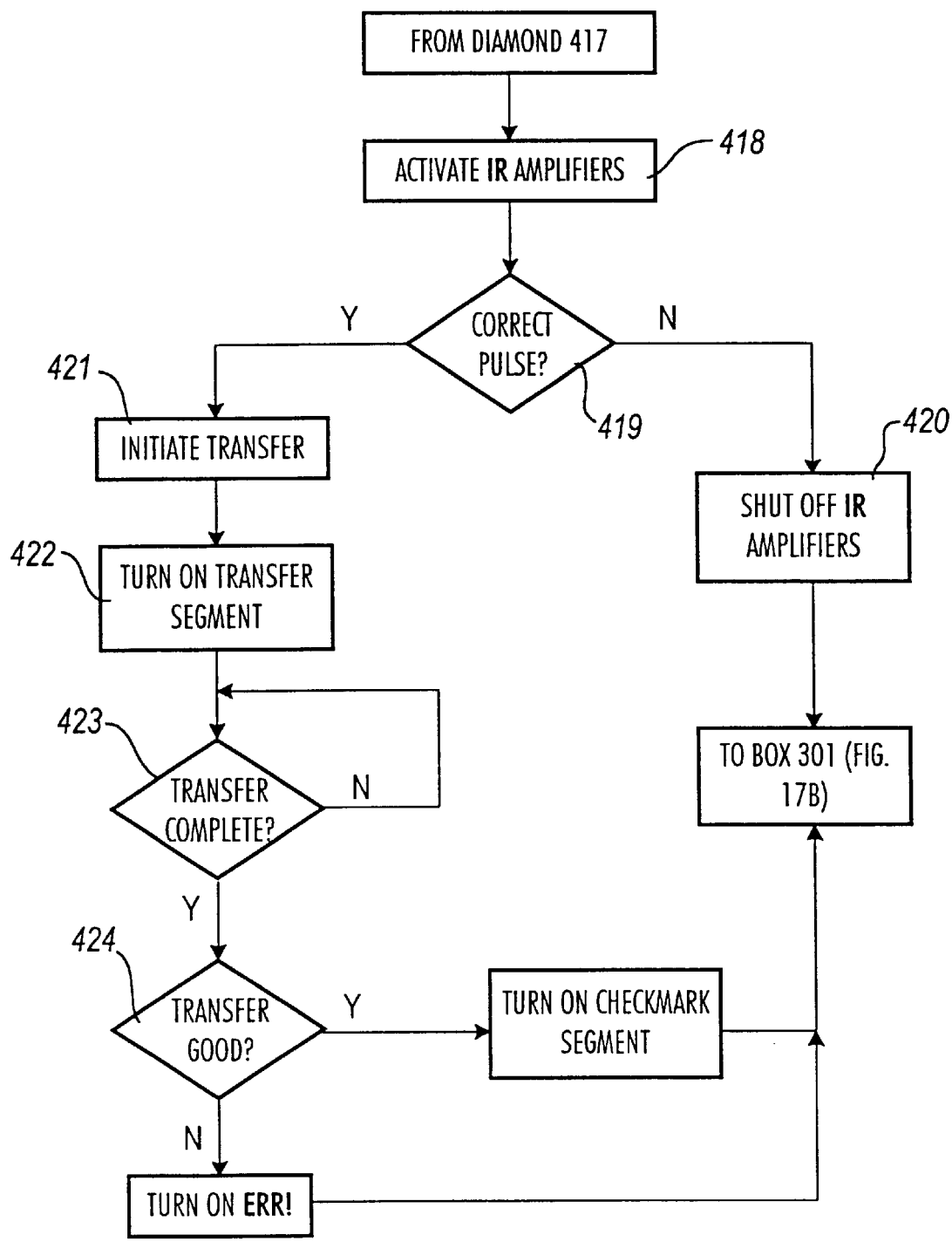
Figure 17F:
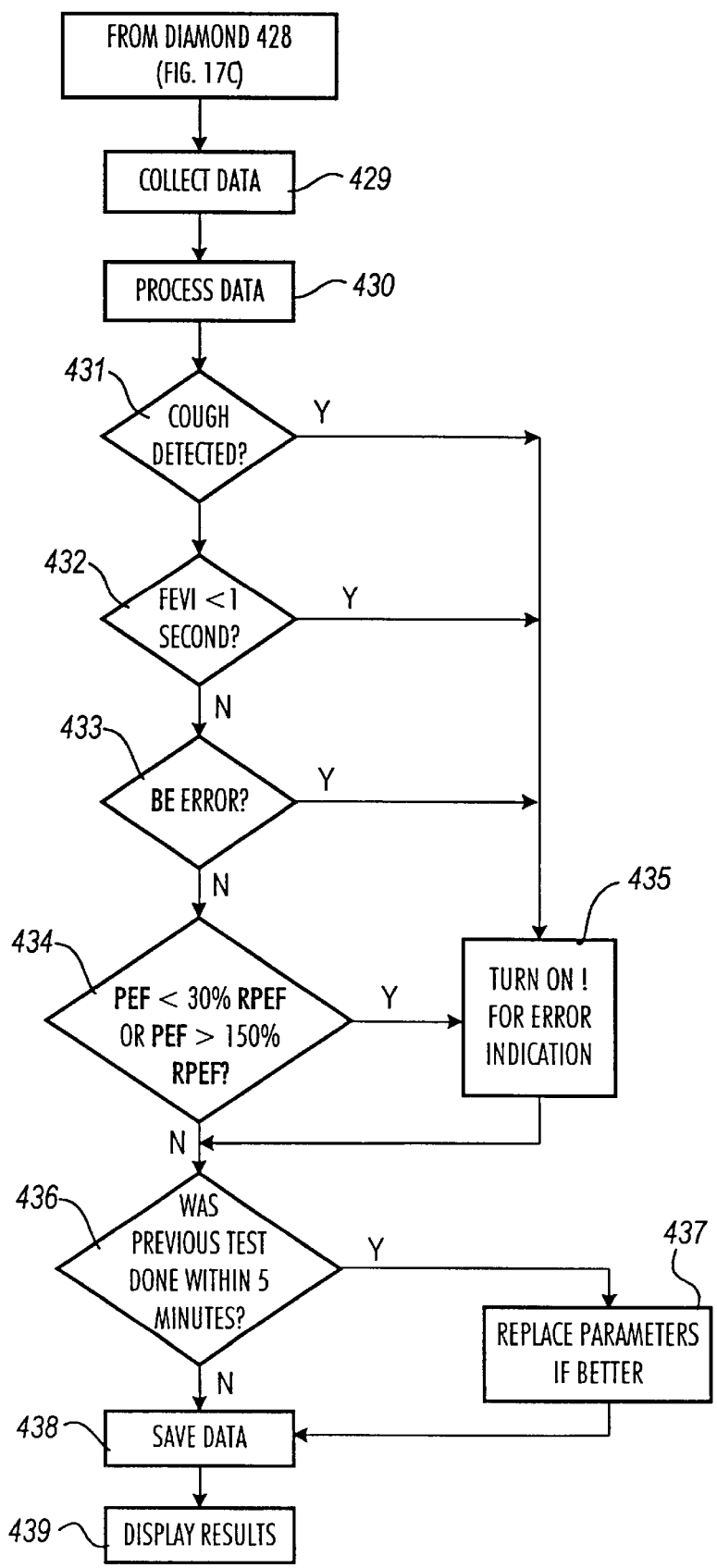
Figure 17G:
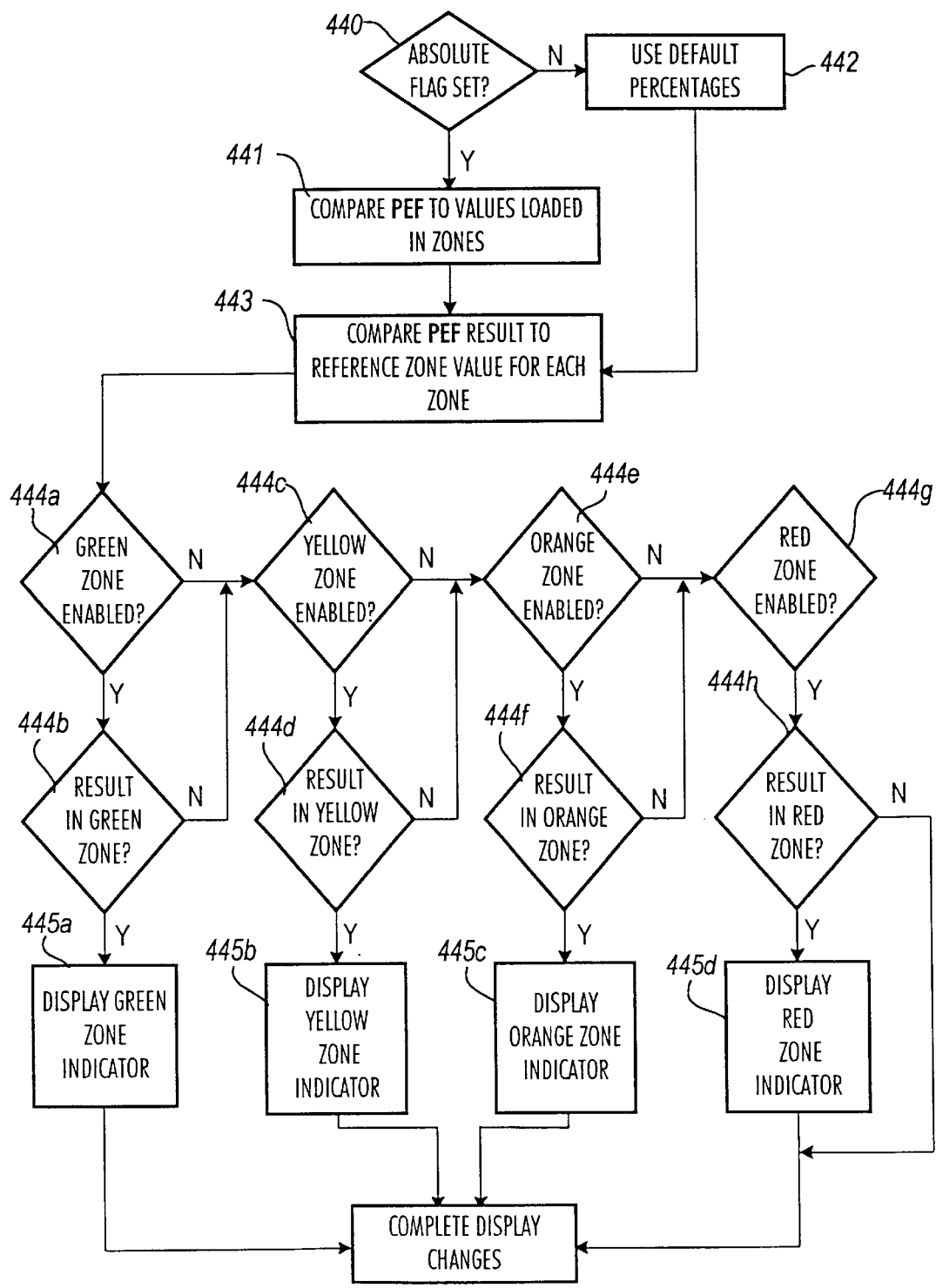

FIG. 17G depicts the process used for displaying the proper zone indicator in segments 301a–d. In decision diamond 440, the microprocessor determines if the absolute flag is set. If so, the microprocessor in box 441 compares the measured PEF directly to the values loaded into the zones. As will be appreciated, the reference value can be not only absolute but also the percent of best PEF or the percent of predetermined normal PEF's. If the absolute flag is not set, the microprocessor loads the percent values rather than absolute values in box 442. In box 443, the microprocessor compares (a) the measured PEF to the reference zone value or (b) the ratio of the PEF to a baseline PEF value to a percentage for each zone. The microprocessor then follows the operations set forth in decision diamonds 444a–h and action boxes 445a–d in activating the correct zone indicator. After completing the pertinent action box 445a–d, the microprocessor completes the display sequence described above and ultimately returns to the standby mode 301.

Figure 17H:
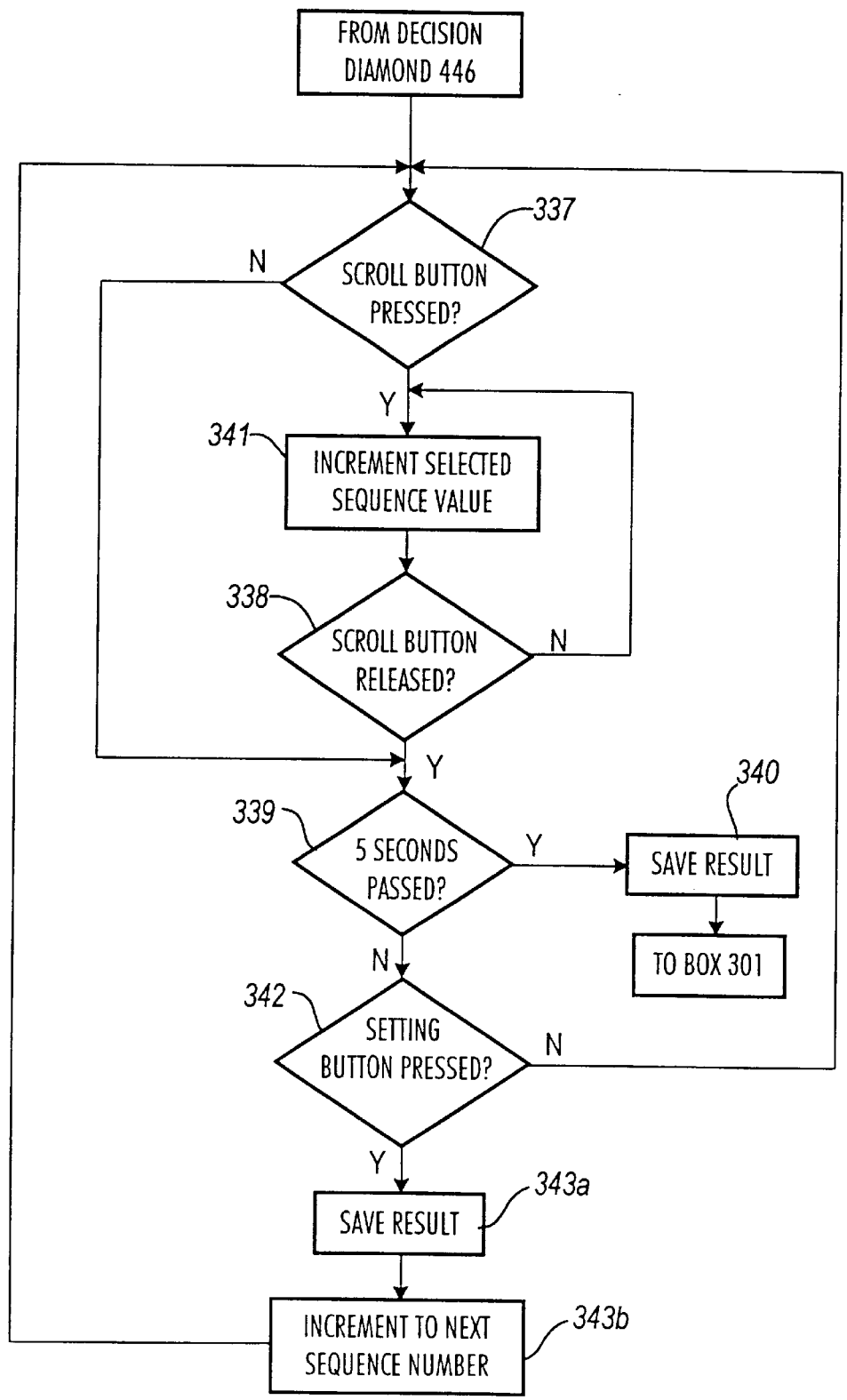
Figure 17I:
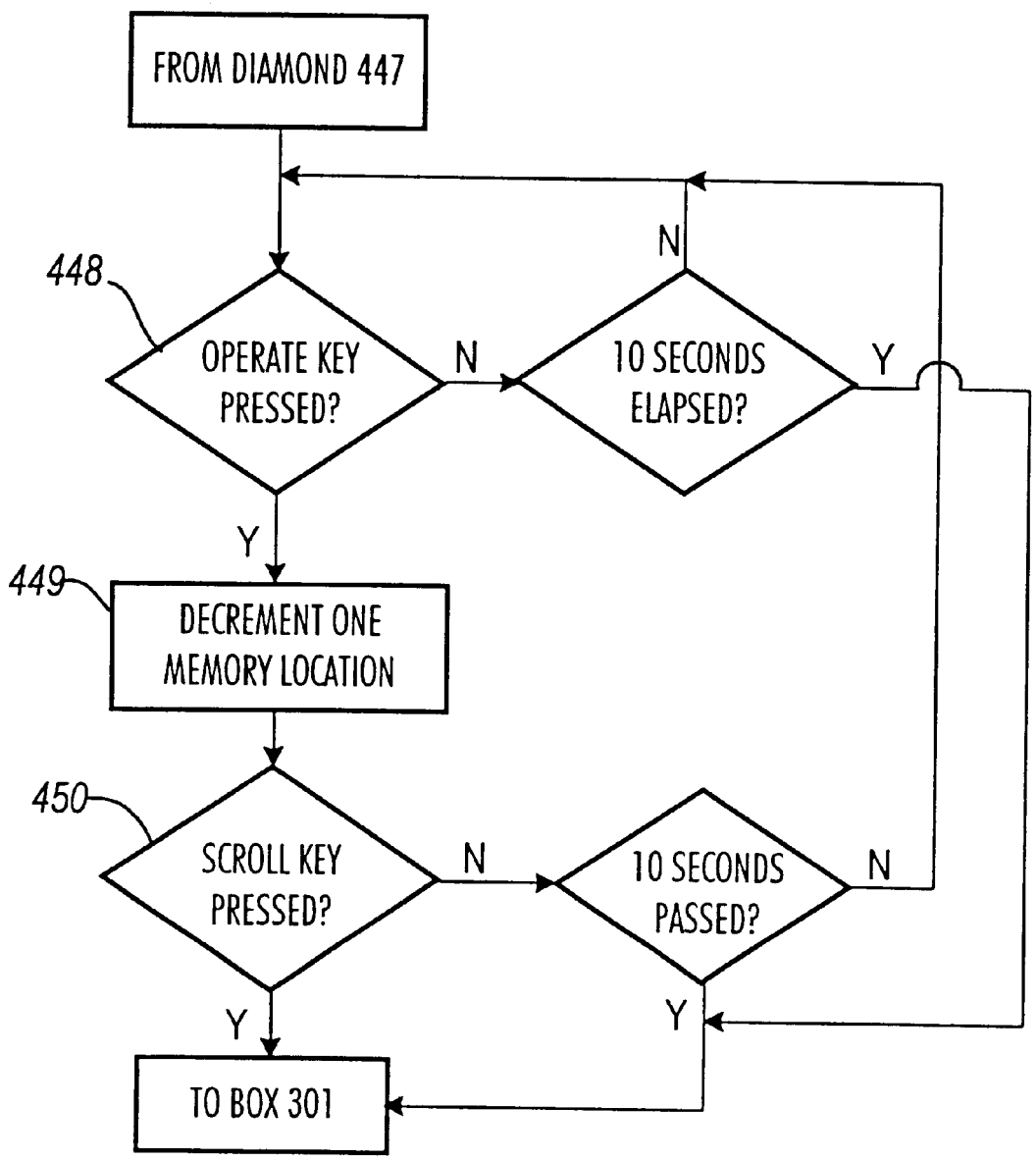

Referring again to FIG. 17B, the microprocessor next determines in decision diamond 446 if the setting key 194c has been pressed for more than three seconds. If so, the microprocessor proceeds to the manual setting mode or subroutine depicted in FIG. 17H. In FIG. 17H, the microprocessor determines in decision diamond 337 if the user has pressed the scroll key 294b. If so, the microprocessor in box 341 increments the selected sequence value (e.g., increments to the next hour). If the scroll key 294b is held down the display scrolls faster then if the scroll key is intermittently pressed. The microprocessor in decision diamond 338 determines if the scroll key 294b is released. If not, the microprocessor loops back to diamond 338. If so, the microprocessor determines if five seconds has passed in decision diamond 339. If so, the result from the current sequence is saved in box 340 and the microprocessor proceeds to box 341. If not, the microprocessor determines in decision diamond 342 if the setting key 294c has been pressed. If so, the microprocessor in box 343a saves the result from the current sequence and in box 343b increments to the next sequence number. If not, the microprocessor returns to decision diamond 337. Using this subroutine, the clock hour and minute; first, second, and third alarm hour and minute; and the reference PEF are set by the user.

Returning to FIG. 17B, the user can enter into a scroll mode or subroutine to scroll through the contents of the memory 270. When the microprocessor determines in decision diamond 447 that the scroll key 194b has been pressed by the user, the microprocessor proceeds to decision diamond 448 in FIG. 17I. If the user has not pressed the operate key 294a, the microprocessor determines if ten seconds has elapsed since the last key was pressed. If so, the microprocessor proceeds to the standby mode 301. If not, the microprocessor loops back to decision diamond 448. If the user has pressed the operate key 294a, the microprocessor in box 449 decrements one memory location and determines in decision diamond 450 whether the scroll key 194b has been pressed. If so, the microprocessor returns to the standby mode 301. If not, the microprocessor determines in decision diamond 451 whether 10 seconds has elapsed. If so, the microprocessor proceeds to box 301 of FIG. 17B. If not, the microprocessor returns to decision diamond 448.

In decision diamond 416, it is determined whether the setting key 94c was pressed for less than three seconds. If so, the microprocessor proceeds to decision diamond 417 where the microprocessor determines if the device is in a cradle (not shown) for uploading or downloading of information from or to another computer (not shown). If the device is not in the cradle, the microprocessor in box 302 activates the segment 316 to signify an error and returns to the standby mode 301.

If the device is in the cradle, the microprocessor proceeds to the data transfer subroutine in FIG. 17E. In FIG. 17E, the microprocessor in box 418 activates the IR amplifiers and checks in decision diamond 419 for the correct pulse. If the correct pulse is not detected, the microprocessor in box 420 deactivates the IR amplifiers and returns to the standby mode 301. If the correct pulse is detected, the information transfer is initiated in box 421, and the transfer segment 314 is activated in box 422. In decision diamond 423, the microprocessor determines if the transfer is completed. If not, the microprocessor loops back to decision diamond 423. If so, the microprocessor proceeds to decision diamond 424 where the microprocessor determines if the transfer was good using a checksum or other approach. If the transfer was good, the checkmark segment 315 is activated and the microprocessor returns to the standby mode 301. If the transfer was not good, the segments 308 and 306 are activated to display ERR!. The microprocessor then returns to the standby mode 301.

If the setting key was not pressed for less than three seconds, the microprocessor proceeds to decision diamond 470 of FIG. 17B and determines if an alarm should be triggered. Referring to FIG. 17K, when one of the three alarms is activated in box 471, the microprocessor in box 472 activates the flashing alarm segment 305a–c that corresponds to the triggered alarm and center 390. In box 473, the microprocessor activates the an audible tone from the buzzer 274. In decision diamond 474, the microprocessor determines if the user has pressed the operator key 194a. If so, the microprocessor returns to the standby mode 301. If not, the microprocessor in decision diamond 475 determines if twenty seconds has elapsed. If not, the microprocessor loops back to decision diamond 474. If so, the microprocessor proceeds to the standby mode 301.

Finally, the microprocessor determines in decision diamond 460 if the battery is low (i.e., the power level is 2.7 volts or less). If so, the low battery segment 317 in box 476 is activated. If not, the microprocessor returns to the standby mode 301.

Figure 17J:
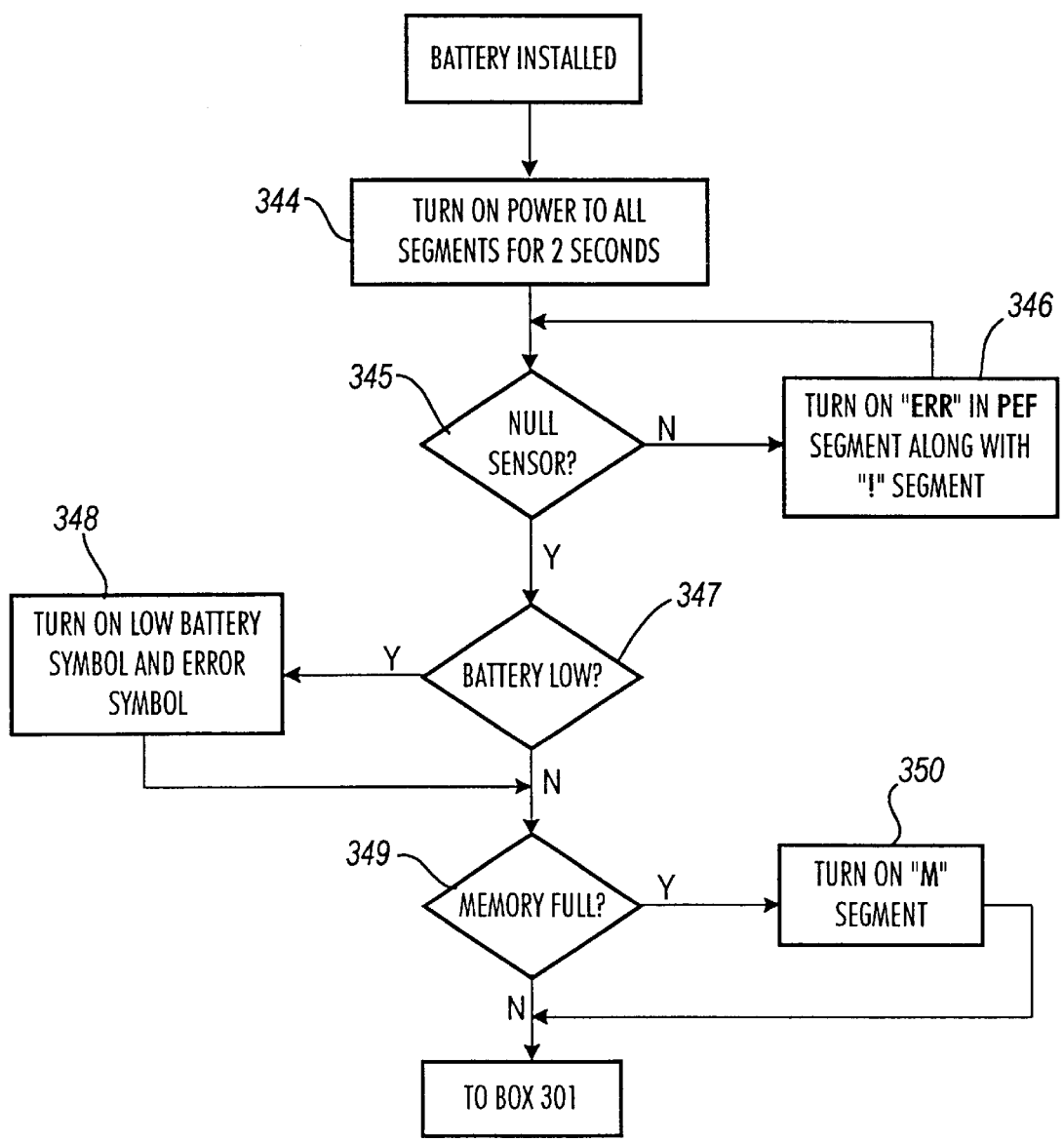
Figure 17K:
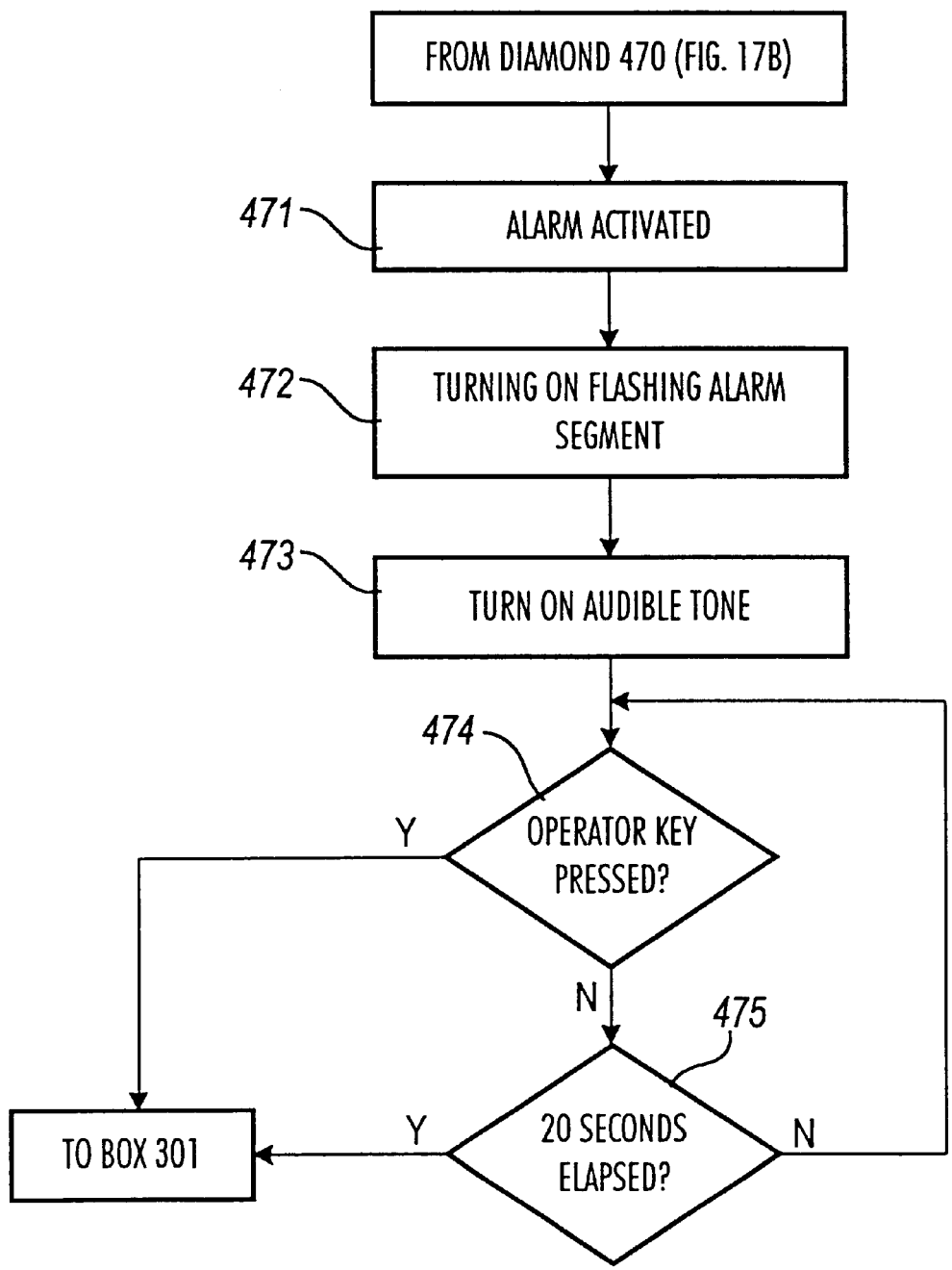

Referring to FIG. 17J, the process used by the microprocessor when the battery is replaced is depicted. Upon installation or replacement of the battery, the microprocessor in box 344 beeps and turns on switches 304a,b for two seconds. The microprocessor in decision diamond 345 then determines if the sensor is nulled. The sensor is nulled when the microprocessor detects a valid signal within two analog-to-digital counts for 16 data points. Before reading the analog-to-digital output, the microprocessor typically waits for a predetermined period to allow the power supply to the amplifier 250 to stabilize. If nulling of the sensor is unsuccessful (e.g., the sensor is not attached, the sensor readings are acceptable, and the reading is stable) the microprocessor proceeds to box 346 activates segments 308 and 306 to display ERR! and returns to decision diamond 345. If the sensor is nulled, the microprocessor proceeds to decision diamond 347 where the microprocessor determines if the battery is low. If so, in box 348 the segments 308 (to show ERR) and 317 are activated for five seconds and the microprocessor proceeds to decision diamond 349. Segment 317 remains activated until power is reset. In decision diamond 349, the microprocessor determines if the memory is full. If so, the M segment 313 is activated in box 350. In either event, the microprocessor proceeds to box 301, which is the standby mode.

The foregoing description of the present invention has been presented for purposes of illustration and description. Furthermore, the description is not intended to limit the invention to the form disclosed herein. Consequently, variations and modifications commensurate with the above teachings, and the skill or knowledge of the relevant art, are within the scope of the present invention.

Figure 19:
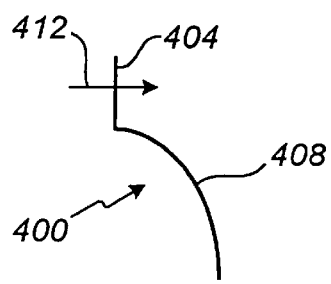
FIGS. 19–22 show differing plate member configurations.
Figure 20:
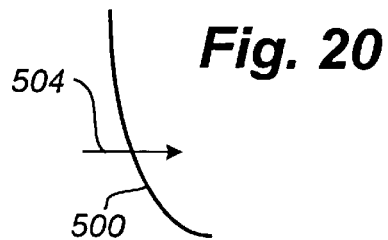
Figure 21:
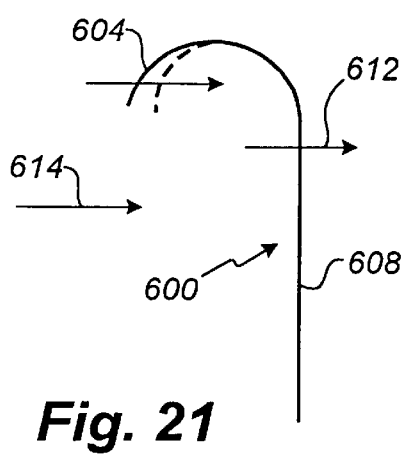
Figure 22:
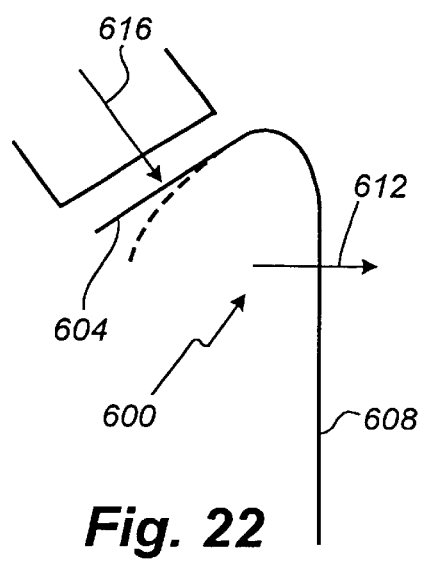

By way of example, the plate member can have any number of a plurality of shapes. In FIG. 19, a plate member 400 includes a straight or flat section 404 on one end and a curvilinear section 408 on the other end that moves in direction 412. FIG. 20 shows a curvilinear plate member 500 that moves in direction 504. In FIG. 21, a plate member 600 is shown that has a curved section 604 and a flat section 608 that are both displaced in direction 612 in response to air flow 614. The curved section 604 is further elastically deformed by the air flow as shown by the dotted line. This plate member configuration is depicted in FIG. 22 interacting with an air flow 616 contacting the plate member 600 at a different angle than that depicted in FIG. 21.

Figure 27:
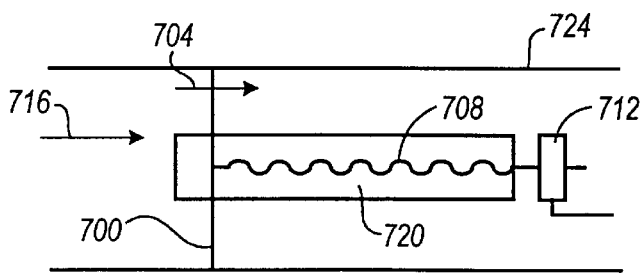
FIG. 27 depicts another configuration of a system for determining the location of the plate member and/or a force applied to the plate member by the airflow.

The plate member can move not only rotatably but also linearly. FIG. 27 shows a configuration in which the plate member 700 moves linearly in direction 704. The plate member 700 is engaged with a spring member 708 that is in turn engaged with a strain gauge 712. As the plate member 700 is displaced by the air flow 716 in direction 704, the spring member 708 causes an increasing force to be applied to the strain gauge, thereby altering the electrical signal output by the gauge. An outlet 720 is located along a wall of the conduit 724 such that as the plate member 700 moves towards the strain gauge 712, the air 716 has an increasing area of the outlet available in which to escape from the conduit 724.

Figure 23:
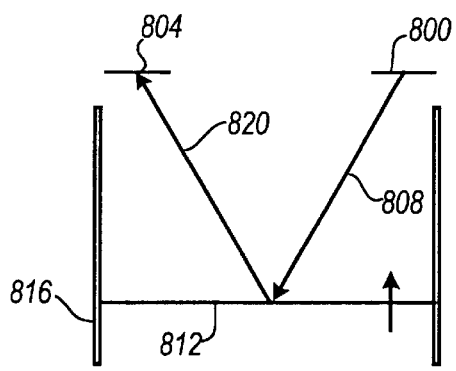
FIG. 23 depicts an alternative configuration for determining the position of the plate member.
Figure 24:
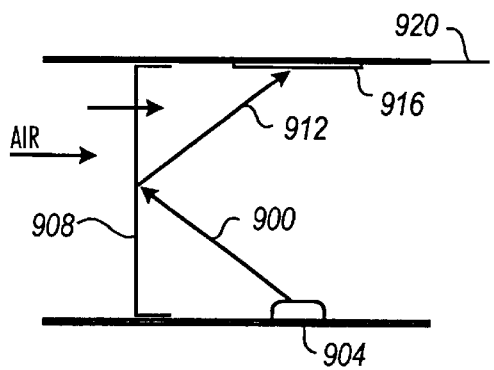
FIG. 24 depicts another alternative configuration for determining the position of the plate member.
Figure 26:
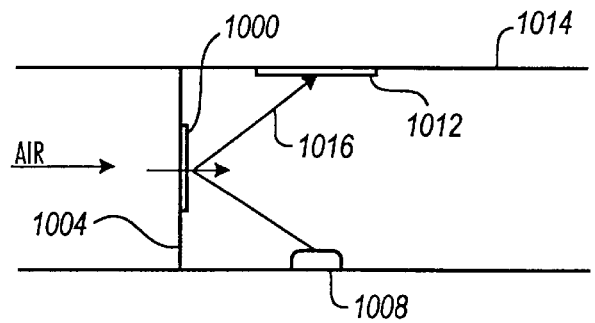
FIGS. 25–26 depict a plate member and a plate member location system according to another alternative configuration, with FIG. 25 being a front view of the plate member and FIG. 26 being a plan view of the system components.
Figure 25:
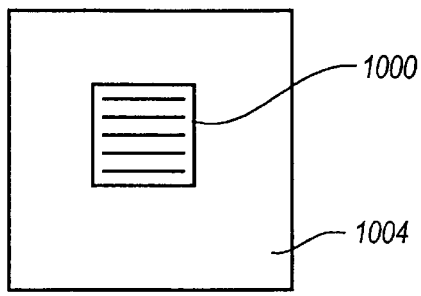

Other techniques are available to monitor the position of the plate member as a function of time. In this manner, the force or pressure exerted by the air flow against the plate member or the flow rate can be determined as a function of time. FIG. 23, for instance, shows an ultrasound transmitter 800, such as one or more piezoelectric crystals, and an ultrasound receiver 804, which can also be one or more piezoelectric crystals. As will be appreciated, one or more piezoelectric crystals can act as both the transmitter or emitter and receiver or detector. An ultrasound beam 808, which can be modulated by known techniques, is transmitted towards the plate member 812 in conduit 816 and reflected off of the plate member 812 and the reflected beam 820 received by the receiver 804. The characteristics of the reflected beam and/or the time duration between signal transmission and reception can be analyzed to determine the distance of the plate member 812 from the ultrasound transmitter 800 and/or receiver (which are typically equidistant from a common plate member surface). FIG. 24 depicts a system in which a light beam 900 is generated and directed by a light emitter 904 towards the plate member 908. The reflected beam 912 is received by a light detector or encoder 916 on a wall of the conduit 920. As in the case of the ultrasound beam, the beam can be modulated. The parts of the detector 916 receiving the reflected beam and/or the characteristics of the reflected beam itself can be used to determine the distance from the light emitter 904 or detector (which is typically the same) to the plate member 908. FIGS. 25 and 26 depict another system using a light beam, which is typically an infrared beam. A bar or interference code 1000 is located on the plate member 1004. The code 1000 causes a unique, detectable reflection pattern depending upon the distance of the code from the light emitter 1008. A detector 1012 mounted on the wall of the conduit 1014 receives the reflected beam 1016 and, based upon the reflected light pattern, is able to determine the distance from the light emitter 1008 or detector (which is typically the same) to the plate member 1004. Additionally, a magnet and a Hall Effect device can be used as described in U.S. Pat. No. 5,277,195, which is incorporated herein by this reference.

Figure 28:
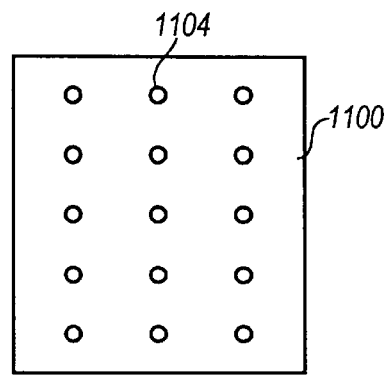
FIG. 28 depicts a plate member and self-oscillating dampener according to another embodiment of the present invention.
Figure 29:
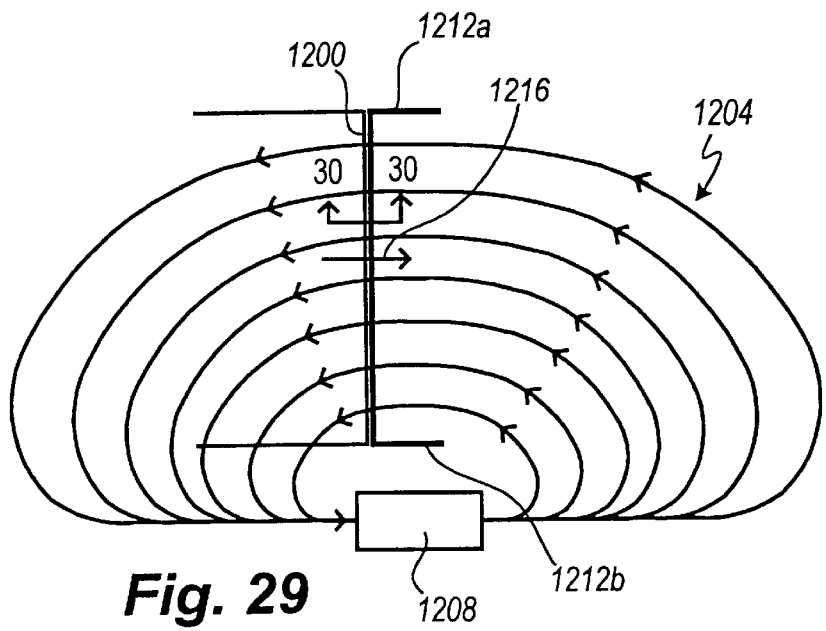
FIGS. 29–30 depict yet another embodiment of a plate member and self-oscillating dampener, with FIG. 29 being a plan view of the system components and FIG. 30 being a side view of the plate member.
Figure 30:
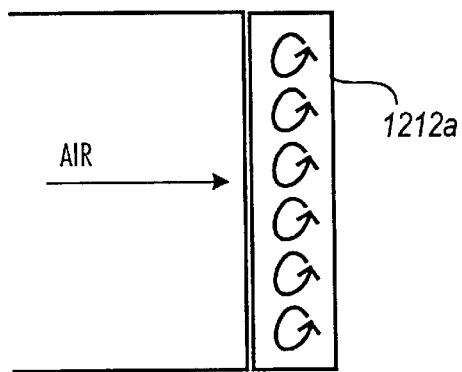

The self-oscillation dampener can be a variety of other systems. FIG. 28 depicts a plate member 1100 that includes a plurality of holes 1104 passing through the plate member 1100. As the plate member 1100 moves in response to exhaled air contacting the front surface of the plate member, air will flow from the area behind the plate member (behind the page of FIG. 28), through the holes 1104, and into the area in front of the plate member 1100 (in front of the page of FIG. 28). In this manner, the amplitude of oscillation of the plate member 1100 is dampened. The holes typically have a diameter ranging from about 0.01 to about 5 mm. FIGS. 29 and 30 depict a method of dampening the amplitudes of oscillations of a plate member 1200 using an electromagnetic field 1204. A strong magnet 1208 is positioned in close proximity to the plate member 1200 (which is metal). The field 1204 induces eddy currents in the side members 1212a,b of the plate member 1200. As will be appreciated, the eddy currents will be in a plane that is normal to the direction of movement 1216 of the plate member 1200. The magnetic field will resist movement of the eddy currents through the field.

Figure 31:
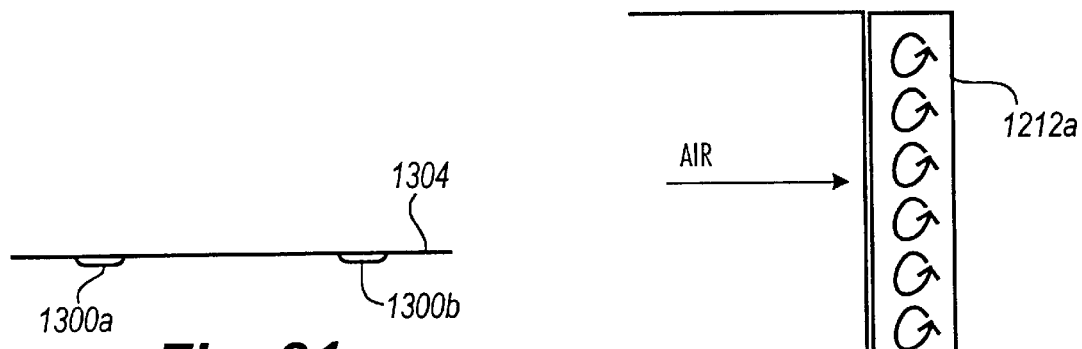
FIG. 31 is a plan view of a plate member according to another embodiment.
Figure 32:
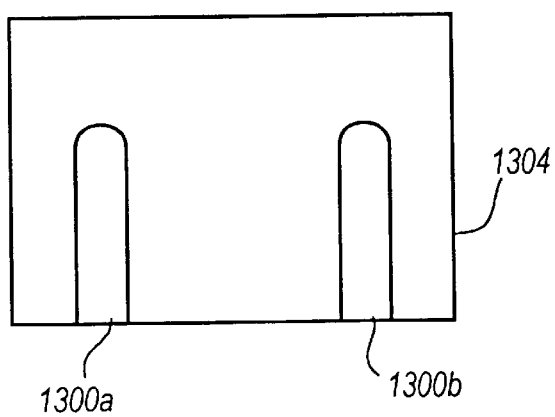
FIG. 32 is a front view of the plate member of FIG. 31.

The stiffening members can be in a variety of configurations. FIGS. 31 and 32 show that the stiffening members can be formed into the plate itself. The members 1300a,b are trough-like depressions in the plane of the plate member 1304. These depressions impart stiffness or rigidity to the plate member 1304. As will be appreciated, the stiffening members can be any other shape or depth of irregularity in the planarity of the plate surface.

The embodiments described herein above are further intended to explain best modes known for practicing the invention and to enable others skilled in the art to utilize the invention in such, or other, embodiments and with various modifications required by the particular applications or uses of the present invention. It is intended that the appended claims be construed to include alternative embodiments to the extent permitted by the prior art.

What is claimed is:

1. A device for measuring respiratory air flow, comprising:
    (a) a conduit having an inlet for exhaled air and an outlet for the exhaled air;
    (b) a sensing member movably disposed in the conduit between the inlet and at least a portion of the outlet, the sensing member at least partially blocking at least a portion of the conduit and moving in response to the passage of the exhaled air through the conduit; and
    (c) a self-oscillation dampener movably engaging the sensing member, wherein the self-oscillation dampener dampens an amplitude of oscillations of the sensing member in response to the exhaled air contacting the sensing member.

2. The device of claim 1, wherein the self-oscillation dampener frictionally resists movement of the sensing member.

3. The device of claim 1, wherein the self-oscillation dampener is inclined at a contact angle relative to the sensing member and the angle is 75° or less.

4. The device of claim 1, wherein the sensing member has a height and the self-oscillation dampener engages the sensing member at a point that is at a distance of at least about 25% and no more than about 95% of the height from a lower edge of the sensing member.

5. The device of claim 1, wherein the sensing member includes or engages one or more stiffening members to provide a desired natural frequency to the sensing member.

6. The device of claim 1, wherein the conduit redirects a direction of flow of the exhaled air such that at the inlet the direction of flow is substantially parallel to a surface of the sensing member and at the sensing member the direction of flow is substantially normal to the surface of the sensing member.

7. The device of claim 1, wherein the self-oscillation dampener has a length and the length ranges from about 10 to about 150% of the height of the sensing member.

8. The device of claim 1, further comprising a measuring device for measuring, as a function of time, at least one of a force applied to the sensing member by the exhaled air and a location of the sensing member, and wherein the measuring device is at least one of a strain gauge and a radiant energy emitter in communication with a radiant energy detector.

9. The device of claim 1, wherein a first end of the self-oscillation dampener movably engages the sensing member and a second end of the self-oscillation dampener fixedly engages a surface of the conduit.

10. A method for measuring respiratory air flow, comprising:
    (a) exhaling air into an inlet of a conduit;
    (b) moving a sensing member that is movably disposed in the conduit downstream of the inlet, the sensing member at least partially blocking the conduit and moving in response to the passage of the exhaled air through the conduit;
    (c) resisting movement of the sensing member with a self-oscillation dampener to dampen amplitudes of oscillations of the sensing member; and
    (d) measuring at least one of a force applied to the sensing member by the exhaled air and the location of the sensing member.

11. The method of claim 10, wherein the measuring step includes:
    contacting the sensing member with a radiant beam; and
    receiving a reflected radiant beam with a detector.

12. The method of claim 11, wherein the sensing member includes a bar code for encoding the reflected radiant beam.

13. The method of claim 10, wherein the sensing member includes one or more stiffening members to control a natural frequency of the sensing member.

14. The method of claim 10, wherein the measuring step includes:
    measuring the location of the sensing member at a plurality of points in time and generating a plurality of location signals; and
    processing the plurality of location signals to determine a desired air flow parameter.

15. A system for measuring respiratory air flow, comprising:
    (a) an inlet of a conduit for receiving exhaled air;
    (b) a plate member that is movably disposed in the conduit downstream of the inlet, the plate member at least partially blocking the conduit and moving in response to the passage of the exhaled air through the conduit;
    (c) a self-oscillation dampener for resisting movement of the plate member to dampen amplitudes of oscillations of the plate member; and
    (d) means for measuring at least one of a force applied to the plate member by the exhaled air and the location of the plate member.

16. The system of claim 15, wherein the self-oscillation dampener is inclined at an angle relative to the plate member and the angle is 75° or less.

17. The system of claim 15, wherein the plate member has a height and the self-oscillation dampener engages the plate at a point that is at distance of at least about 25% and no more than about 95% of the height from a lower edge of the plate member.

18. The system of claim 15, wherein the plate member includes or engages one or more stiffening members to impart rigidity to the plate member.

19. The system of claim 15, wherein the conduit redirects a direction of flow of the exhaled air such that at the inlet the direction of flow is substantially parallel to a plane of the plate member and at the plate member the direction of flow is substantially normal to the plane of the plate member.

20. The system of claim 15, wherein the self-oscillation dampener has a length and the length ranges from about 10 to about 150% of the height of the plate member.

21. The system of claim 15, wherein the measuring means is at least one of a strain gauge and a radiant energy emitter in communication with a radiant energy detector.

22. The system of claim 15, wherein the self-oscillation dampener frictionally resists movement of the plate member.

23. A device for measuring respiratory air flow, comprising:
(a) a conduit having an inlet for exhaled air and an outlet for the exhaled air;
(b) a plate member movably disposed in the conduit between the inlet and outlet, the plate member at least partially blocking the conduit and moving in response to passage of the exhaled air through the conduit, wherein the plate member is perforated to maintain a resonant frequency of the plate member above a selected level, wherein the selected level is higher than a frequency of oscillations imparted to the plate member by the exhaled air; and
(c) an air flow measuring device for measuring the air flow through the conduit.

24. The device of claim 23, further comprising one or more stiffening members located at one or more peripheral edges of the plate member.

25. The device of claim 24, wherein the one or more stiffening members are located on a downstream surface of the plate member relative to the direction of exhaled air flow.

26. The device of claim 23, further comprising a self-oscillation dampener for controlling amplitudes of oscillations of the plate member.

27. The device of claim 23, wherein the conduit redirects a direction of flow of the exhaled air such that at the inlet the direction of flow is substantially parallel to a plate of the plate member and at the plate member the direction of flow is substantially normal to the plane of the plate member.

28. A method for measuring respiratory air flow, comprising:
(a) exhaling air into an inlet of a conduit;
(b) moving a plate member that is movably disposed in the conduit downstream of the inlet, the plate member at least partially blocking the conduit and moving in response to the passage of the exhaled air through the conduit, wherein the plate member includes a plurality of holes passing therethrough;
(c) passing air located on a first side of the plate member through the plurality of holes to maintain a resonant frequency of the plate member at or above a selected level, wherein the exhaled air contacts a second side of the plate member that is opposite to the first side of the plate member, and wherein the selected level is higher than a frequency of oscillations imparted to the plate member by the exhaled air; and
(d) measuring at least one of a force and a pressure applied to the plate member by the exhaled air and the location of the plate member.

29. The method of claim 28, wherein the measuring step includes:
contacting the plate member with a radiant beam; and
receiving a reflected radiant beam with a detector.

30. The method of claim 29, wherein the plate member includes a bar code for encoding the reflected radiant beam.

31. The method of claim 29, further comprising a self-oscillation dampener to control an amplitude of oscillations of the plate member.

32. The method of claim 28, wherein the measuring step includes:
measuring the location of the plate member at a plurality of points in time and generating a plurality of location signals; and
processing the plurality of location signals to determine a desired air flow parameter.

33. The method of claim 28, wherein said at least one of a force and a pressure is a force.

34. A device for measuring respiratory air flow, comprising:
(a) a conduit having an inlet for exhaled air and an outlet for the exhaked air; and
(b) a sensing member for measuring an air flow parameter, wherein a first direction of air flow through the inlet is transverse to a second direction of air flow at the sensing member, wherein a third direction of air flow at the outlet located downstream of the sensing member is transverse to the first and second directions of flow, and wherein the sensing member is movably disposed in the conduit between the inlet and the outlet, the sensing member at least partially blocking the conduit and moving in response to the passage of the exhaled air through the conduit.

35. The device of claim 34, wherein the sensing member includes one or more stiffening members to control a resonant frequency of the sensing member.

36. The device of claim 34, further comprising a self-oscillation dampener for controlling an amplitude of oscillations of the sensing member.

37. The device of claim 36, wherein the self-oscillation dampener includes at least one of a plurality of holes in the sensing member and a plurality of eddy currents in a portion of the sensing member, the eddy currents being imparted to the sensing member by an electromagnetic field.

38. The device of claim 34, wherein a plane defined by a face of the sensing member is substantially parallel to the first direction of air flow.

39. The device of claim 34, wherein a plane of movement of the sensing member is transverse to the first direction of air flow.

40. A method for measuring respiratory air flow, comprising:
(a) passing exhaled air through an inlet of a conduit, the exhaled air having a first direction of flow through the inlet;
(b) contacting the exhaled air with a moveable sensing member located in the conduit between the inlet and an outlet, the exhaled air having a second direction flow adjacent to the sensing member and the sensing member at least partially blocking the conduit and moving in response to the passage of the exhaled air through the conduit;

(c) measuring an air flow parameter using a signal generated in response to movement of the sensing member in the conduit between the inlet and outlet, wherein the first direction of flow is transverse to the second direction of flow; and (d) passing the exhaled air through the outlet, the outlet being located downstream of the sensing member, wherein a third direction of flow of the exhaled air at the outlet is transverse to the first and second directions of flow.

41. The method of claim 40, wherein the measuring step includes:

contacting the sensing member with a radiant beam; and receiving a reflected beam with a detector.

42. The method of claim 41, wherein the sensing member includes a bar code for encoding the reflected radiant beam.

43. The method of claim 40, further comprising a self-oscillation dampener to control an amplitude of oscillations of the sensing member.

44. The method of claim 40, wherein the first direction of flow is substantially normal to the second direction of flow.

45. The method of claim 40, wherein the measuring step includes:

measuring the location of the sensing member at a plurality of points in time and generating a plurality of location signals; and processing the plurality of location signals to determine a desired air flow parameter.

46. A device for measuring respiratory air flow, comprising:

(a) a conduit having an inlet for exhaled air and an outlet for the exhaled air;

(b) a plate member movably disposed in the conduit between the inlet and the outlet, the plate member at least partially blocking the conduit and moving in response to the passage of the exhaled air through the conduit, wherein movement of the plate member permits the exhaled air to flow around the plate member; and (c) a measuring device for measuring at least one of a pressure and a force applied against the plate member by the exhaled air and generating a measurement signal, the measuring device being located on the plate member.

47. The device of claim 46, wherein said at least one of a pressure and a force is a force.

48. The device of claim 46, wherein the plate member includes one or more stiffening members to control a resonant frequency of the plate member.

49. The device of claim 46, further comprising a self-oscillation dampener for controlling an amplitude of oscillations of the plate member.

50. The device of claim 49, wherein the self-oscillation dampener includes at least one of a plurality of holes in the plate member and a plurality of eddy currents in a portion of the plate member, the eddy currents being imparted to the plate member by an electromagnetic field.

51. The device of claim 46, wherein an orifice is located between the plate member and a wall of the conduit, the exhaled air having a first direction of flow at the inlet and a second direction of flow at the orifice and the first direction of flow is transverse to the second direction of flow.

52. The device of claim 51, wherein a plane defined by a face of the plate member is substantially parallel to the first direction of air flow at the inlet.

53. The device of claim 51, wherein a plane of movement of the plate member is transverse to the first direction of air flow at the inlet.

54. A device for measuring respiratory air flow, comprising:

(a) a conduit having an inlet for exhaled air and an outlet for the exhaled air;

(b) a sensing member movably disposed in the conduit between the inlet and the outlet, the sensing member at least partially blocking the conduit and moving in response to the passage of the exhaled air through the conduit; and (c) a measuring device for measuring, at a plurality of points in time, the location of the sensing member and generating a plurality of location signals wherein the measuring device includes a sound emitter in communication with a sound detector; and (d) a processing unit, in communication with the measuring device, for receiving the plurality of location signals and determining a plurality of positions of the sensing member that correspond to the plurality of location signals.

55. The device of claim 54, further comprising:

(e) an electronic memory, in communication with the processing unit, for recording the plurality of locations at the plurality of points in time.

56. The device of claim 54, wherein the conduit redirects a direction of flow of the exhaled air such that at the inlet the direction of flow is substantially parallel to a surface of the sensing member and at the sensing member the direction of flow is substantially normal to the surface of the sensing member.

57. The device of claim 54, further comprising a self-oscillation dampener to resist movement of the sensing member.

58. The device of claim 54, wherein the sound is emitted as ultrasound energy.

59. The device of claim 54, wherein the sensing member includes or engages one or more stiffening members to impart rigidity to the sensing member.

60. The device of claim 59, wherein the one or more stiffening members are located on a downstream surface of the sensing member relative to the direction of exhaled air flow.

61. A method for determining exhaled air flow, comprising:

(a) exhaling air into an inlet of a conduit;

(b) moving a sensing member that is movably disposed in the conduit downstream of the inlet, the sensing member at least partially blocking the conduit and moving in response to the passage of the exhaled air through the conduit;

(c) emitting sound energy;

(d) receiving reflected sound energy that is reflected by the sensing member;

(e) determining a location of the sensing member and generating a location signal; and (f) processing the location signal to determine a desired air flow parameter.

62. The method of claim 61, further comprising a self-oscillation dampener to control an amplitude of oscillation of the sensing member.

63. The method of claim 61, wherein the sound energy is emitted by one or more piezoelectric crystals.

64. The system of claim 61, wherein the sound energy is modulated.

65. The method of claim 61, wherein the conduit redirects a direction of flow of the exhaled air such that at the inlet the direction of flow is substantially parallel to a surface of the sensing member and at the sensing member the direction of flow is substantially normal to the surface of the sensing member.

66. The method of claim 61, wherein the receiving step includes:

contacting the sensing member with sound energy; and receiving the reflected sound energy with a detector.

67. The method of claim 66, wherein the sensing member includes a bar code for encoding the reflected sound energy beam.

68. The method of claim 61, wherein the sensing member includes one or more stiffening members to control a resonant frequency of the sensing member.

69. A device for measuring respiratory air flow, comprising:

(a) a conduit having an inlet for exhaled air and an outlet for the exhaled air; and (b) a sensing member for measuring an air flow parameter, wherein a direction of air flow through the inlet is transverse to a direction of air flow at the sensing member, wherein the sensing member is movably disposed in the conduit between the inlet and outlet, the sensing member at least partially blocking the conduit and moving in response to the passage of the exhaled air through the conduit, and wherein the sensing member includes one or more stiffening members to control a resonant frequency of the sensing member.

70. The device of claim 69, further comprising a self-oscillation dampener for controlling an amplitude of oscillations of the sensing member.

71. The device of claim 70, wherein the self-oscillation dampener includes at least one of a plurality of holes in the sensing member, and a plurality of eddy currents in a portion of the sensing member, the eddy currents being imparted to the sensing member by an electromagnetic field.

72. The device of claim 69, wherein a plane defined by a face of the sensing member is substantially parallel to the direction of air flow at the inlet.

73. The device of claim 69, wherein a plane of movement of the sensing member is transverse to the direction of air flow at the inlet.

74. A device for measuring respiratory air flow, comprising:

(a) a conduit having an inlet for exhaled air and an outlet for the exhaled air;

(b) a sensing member for measuring an air flow parameter, wherein a direction of air flow through the inlet is transverse to a direction of air flow at the sensing member and wherein the sensing member is movably disposed in the conduit between the inlet and outlet, the sensing member at least partially blocking the conduit and moving in response to the passage of the exhaled air through the conduit; and (c) a self-oscillation dampener for controlling an amplitude of oscillations of the sensing member.

75. The device of claim 74, wherein the sensing member includes one or more stiffening members to control a resonant frequency of the sensing member.

76. The device of claim 74, wherein the self-oscillation dampener includes at least one of a plurality of holes in the sensing member, and a plurality of eddy currents in a portion of the sensing member, the eddy currents being imparted to the sensing member by an electromagnetic field.

77. The device of claim 74, wherein a plane defined by a face of the sensing member is substantially parallel to the direction of air flow through the inlet.

78. The device of claim 74, wherein a plane of movement of the sensing member is transverse to the direction of air flow through the inlet.

79. A device for measuring respiratory air flow, comprising:

(a) a conduit having an inlet for exhaled air and an outlet for the exhaled air;

(b) a plate member movably disposed in the conduit between the inlet and the outlet, the plate member at least partially blocking the conduit and moving in response to the passage of the exhaled air through the conduit; and (c) a measuring device for measuring at least one of a pressure and a force applied against the plate member by the exhaled air and generating a measurement signal, the measuring device being located on the plate member, wherein an orifice is located between the plate member and a wall of the conduit, wherein the exhaled air has a first direction of flow at the inlet and a second direction of flow at the orifice and the first direction of flow is transverse to the second direction of flow, and wherein a plane defined by a face of the plate member is substantially parallel to the first direction of air flow at the inlet.

80. The device of claim 79, wherein said at least one of a pressure and a force is a force.

81. A device for measuring respiratory air flow, comprising:

(a) a conduit having an inlet for exhaled air and an outlet for the exhaled air;

(b) a plate member movably disposed in the conduit between the inlet and the outlet, the plate member at least partially blocking the conduit and moving in response to the passage of the exhaled air through the conduit; and (c) a measuring device for measuring at least one of a pressure and a force applied against the plate member by the exhaled air and generating a measurement signal, the measuring device being located on the plate member, wherein an orifice is located between the plate member and a wall of the conduit, wherein the exhaled air has a first direction of flow at the inlet and a second direction of flow at the orifice and the first direction of flow is transverse to the second direction of flow, and wherein a plane of movement of the plate member is transverse to the first direction of air flow at the inlet.

82. The device of claim 81, wherein said at least one of a pressure and force is a force.

* * * * *